US012778228B2

(12) United States Patent
Berns et al.

(10) Patent No.: US 12,778,228 B2
(45) Date of Patent: Nov. 3, 2026

(54) GARMENT WITH COMPRESSION ADJUSTMENT ARRANGEMENT

(71) Applicant: Under Armour, Inc., Baltimore, MD (US)

(72) Inventors: Jason Berns, Baltimore, MD (US); Mari Lucero, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

(21) Appl. No.: 19/253,933

(22) Filed: Jun. 29, 2025

(65) Prior Publication Data

US 2025/0325060 A1 Oct. 23, 2025

Related U.S. Application Data

(63) Continuation of application No. 17/845,095, filed on Jun. 21, 2022, now Pat. No. 12,342,888, which is a (Continued)

(51) Int. Cl.
*A41D 31/18* (2019.01)
*A41D 1/06* (2006.01)
(Continued)

(52) U.S. Cl.
CPC ............ *A41D 31/185* (2019.02); *A41D 1/06* (2013.01); *A41D 13/0015* (2013.01); (Continued)

(58) Field of Classification Search
USPC ..................................................... 602/19, 26
See application file for complete search history.

(56) References Cited

U.S. PATENT DOCUMENTS

| | | | |
|---|---|---|---|
| 1,391,563 A | 9/1921 | Monin | |
| 2,887,114 A | 5/1959 | Baxter | |

(Continued)

FOREIGN PATENT DOCUMENTS

| | | | |
|---|---|---|---|
| EP | 3636097 A1 * | 4/2020 | ............. A43C 11/00 |
| GB | 2420486 A | 5/2006 | |
| GB | 2542839 A | 4/2017 | |

OTHER PUBLICATIONS

Matweb, Overview of Materials for Nylon 66, Mineral Filled, Impact Grade https://www.matweb.com/search/datasheet_print.aspx?matguid=dd28026cc5804fa08d8369184d157983.*

*Primary Examiner* — Kim M Lewis
(74) *Attorney, Agent, or Firm* — Maginot, Moore & Beck, LLP

(57) ABSTRACT

A garment configured to be worn on a human body is disclosed herein. In at least one embodiment, the garment is a short that includes at least one fabric portion and a compression adjustment arrangement. The least one fabric portion is comprised of an elastic material and is configured to provide a degree of compression to a human body part depending on a degree of stretch of the at least one fabric portion. The at least one fabric portion extends from a hip portion to a limb portion of the short. The compression adjustment arrangement is coupled to the at least one fabric portion. The compression adjustment arrangement includes a first lacing guide, a second lacing guide and a dial. Rotation of the dial is configured to move the first lacing guide toward the second lacing guide and increase an amount of compression provided by the elastic material.

20 Claims, 32 Drawing Sheets

Related U.S. Application Data continuation of application No. 16/718,289, filed on Dec. 18, 2019, now Pat. No. 11,388,943, which is a continuation of application No. 15/096,573, filed on Apr. 12, 2016, now Pat. No. 10,517,335, which is a continuation of application No. 14/066,019, filed on Oct. 29, 2013, now Pat. No. 9,320,307, which is a continuation of application No. 12/815,019, filed on Jun. 14, 2010, now Pat. No. 8,597,222.

(60) Provisional application No. 61/186,500, filed on Jun. 12, 2009.

(51) Int. Cl.

| | |
|---|---|
| ***A41D 13/00*** | (2006.01) |
| ***A41D 13/015*** | (2006.01) |
| ***A41D 15/00*** | (2006.01) |
| ***A41D 27/20*** | (2006.01) |
| ***A41D 31/00*** | (2019.01) |
| ***A61F 13/08*** | (2006.01) |

(52) U.S. Cl.

CPC ......... *A41D 13/0155* (2013.01); *A41D 15/00* (2013.01); *A41D 27/20* (2013.01); *A41D 31/00* (2013.01); *A61F 13/085* (2013.01); *A41D 2400/38* (2013.01)

(56) References Cited

U.S. PATENT DOCUMENTS 3,128,514 A 4/1964 Parker et al.
3,480,012 A 11/1969 Smithers et al.
3,902,503 A 9/1975 Gaylord, Jr.
4,649,574 A 3/1987 Michels
4,677,699 A 7/1987 Barabe
4,697,592 A 10/1987 Maddux et al.
4,737,994 A 4/1988 Galton
4,993,409 A 2/1991 Grim
5,161,257 A 11/1992 Arensdorf
5,170,505 A 12/1992 Rohrer
5,253,435 A 10/1993 Auger et al.
5,267,928 A * 12/1993 Barile ................ A63B 21/4025 2/70
5,334,135 A 8/1994 Grim
5,383,893 A 1/1995 Daneshvar
5,423,852 A 6/1995 Daneshvar
5,435,015 A 7/1995 Ellis-Brewer
5,551,082 A 9/1996 Stewart et al.
5,599,290 A 2/1997 Hayes et al.
5,688,137 A 11/1997 Bustance
5,708,977 A 1/1998 Morkunas
5,795,316 A 8/1998 Gaylord
5,916,070 A 6/1999 Donohue
5,934,599 A * 8/1999 Hammerslag .......... A43C 11/00 242/396.2
5,968,002 A * 10/1999 Morrisseau ........... A61F 5/0102 128/869
6,029,273 A 2/2000 Donohue
RE36,905 E 10/2000 Noble et al.
6,156,001 A 12/2000 Frangi et al.
6,182,288 B1 2/2001 Kibbee
6,227,937 B1 5/2001 Principe
6,289,558 B1 9/2001 Hammerslag
6,338,723 B1 1/2002 Carpenter et al.
6,425,876 B1 7/2002 Frangi et al.
6,652,596 B2 11/2003 Smith et al.
6,688,943 B2 2/2004 Nagaoka
7,087,032 B1 8/2006 Ikeda
7,137,973 B2 11/2006 Plauche et al.
7,476,185 B2 1/2009 Drennan
8,597,222 B2 12/2013 Lucero
9,320,307 B2 4/2016 Berns et al.
10,517,335 B2 12/2019 Berns et al.
2003/0125705 A1 7/2003 Ruman et al.
2004/0002288 A1 1/2004 Bell et al.
2005/0177920 A1 8/2005 Wilkinson
2006/0156517 A1 7/2006 Hammerslag et al.
2007/0169378 A1 7/2007 Sodeberg et al.
2008/0066272 A1 3/2008 Hammerslag et al.
2008/0243041 A1* 10/2008 Brenner ................. A61H 7/004 601/134
2008/0249448 A1* 10/2008 Stevenson ............. A61F 5/0125 602/5
2009/0019734 A1 1/2009 Reagan et al.
2009/0025115 A1 1/2009 Duffy et al.
2009/0192433 A1 7/2009 Wells et al.
2010/0000547 A1 1/2010 Johnson et al.
2010/0037369 A1 2/2010 Reichert
2010/0042026 A1 2/2010 Kloecker
2010/0198122 A1 8/2010 Freund
2011/0264021 A1 10/2011 Hettich
2015/0032041 A1 1/2015 Ingimundarson et al.

* cited by examiner

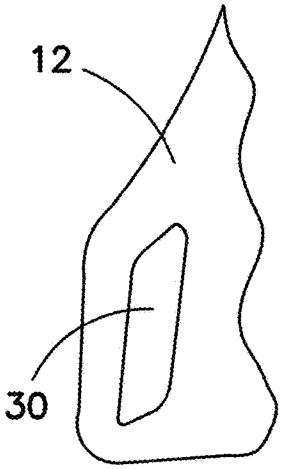
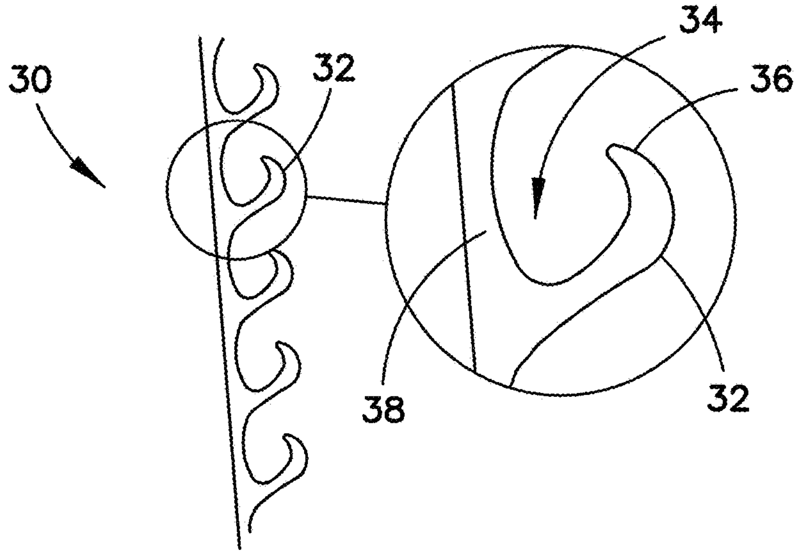
FIG. 2A
FIG. 1C
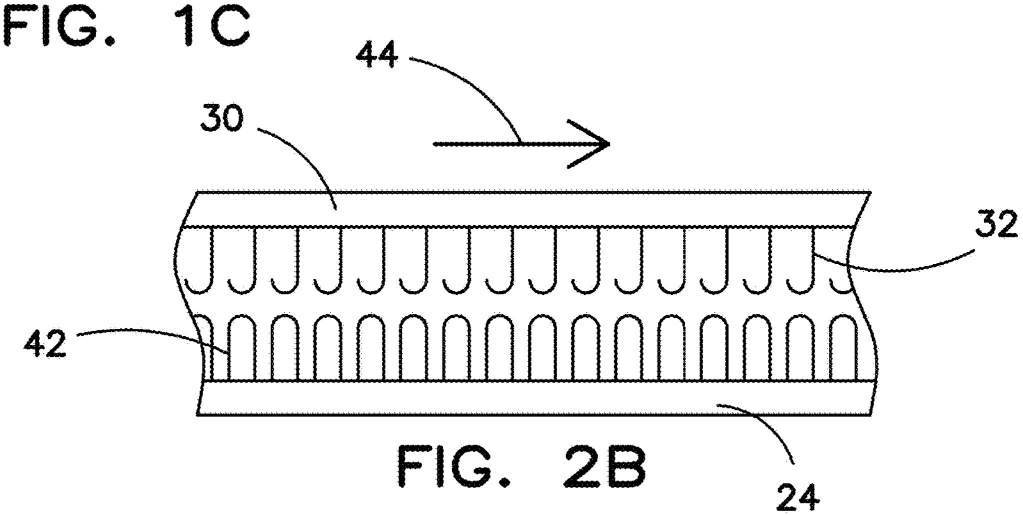
FIG. 2B
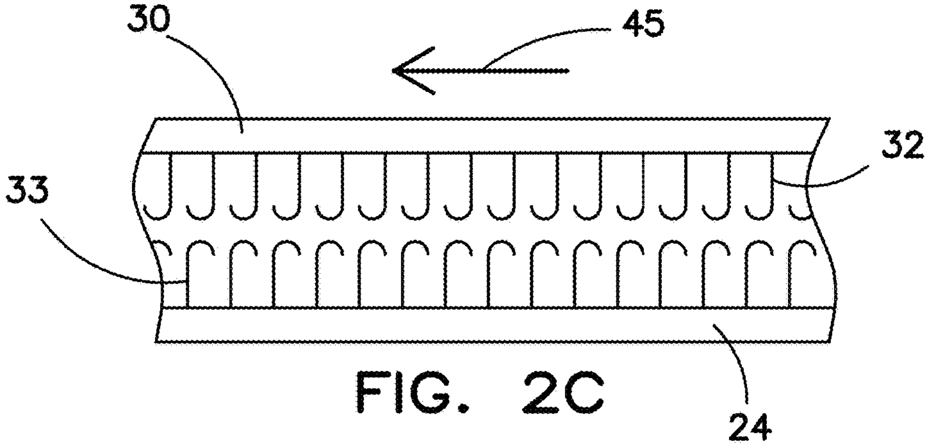
FIG. 2C

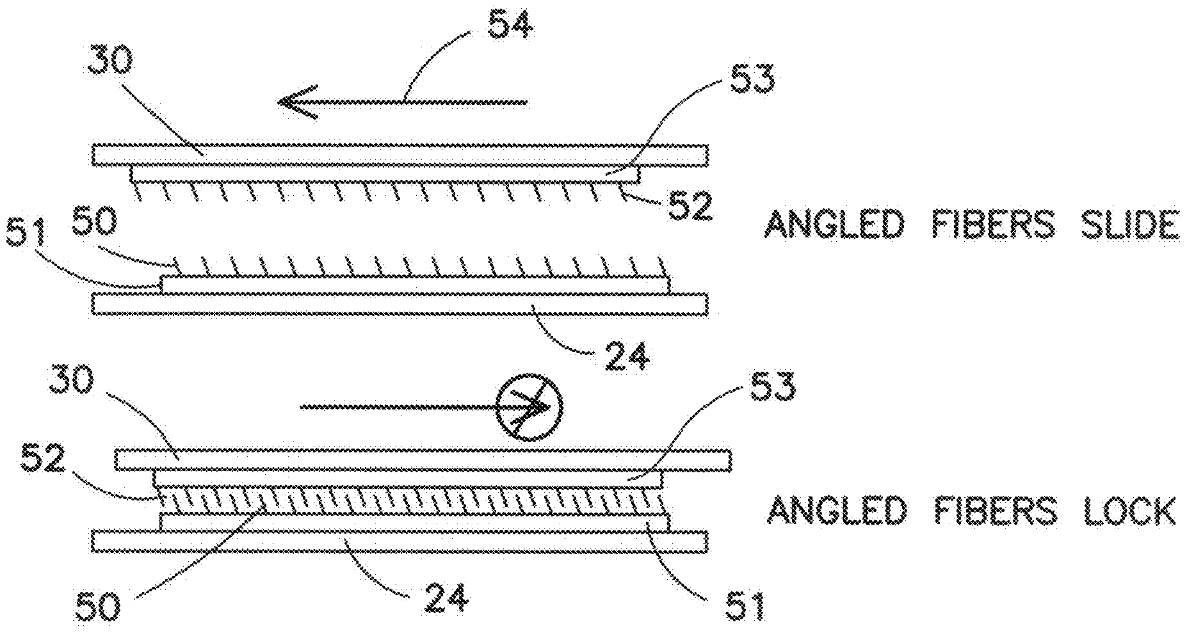
FIG. 3A
FIG. 3B
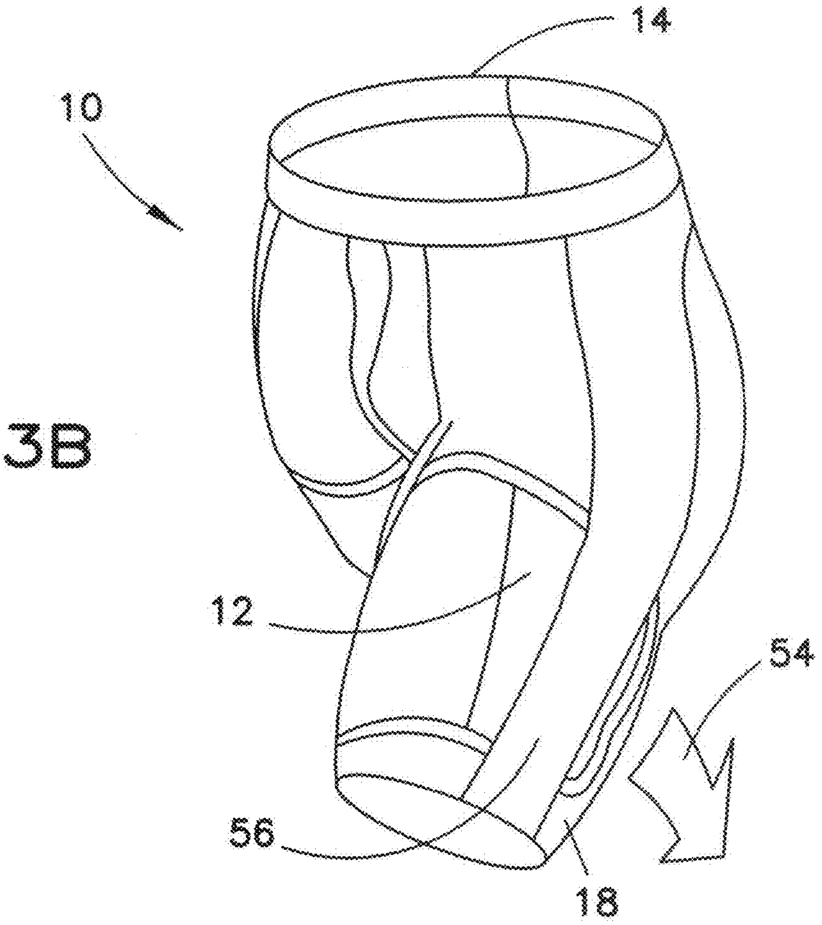

GARMENT WITH COMPRESSION ADJUSTMENT ARRANGEMENT

CROSS-REFERENCE TO RELATED APPLICATIONS

This patent document is a continuation of and claims priority from U.S. patent application Ser. No. 17/845,095, filed Jun. 21, 2022, now U.S. Pat. No. 12,342,888, which is a continuation of and claims priority from U.S. patent application Ser. No. 16/718,289, filed Dec. 18, 2019, now U.S. Pat. No. 11,388,943, which is a continuation of and claims priority from U.S. patent application Ser. No. 15/096,573, filed Apr. 12, 2016, now U.S. Pat. No. 10,517,335, which is a continuation of and claims priority from U.S. patent application Ser. No. 14/066,019, filed Oct. 29, 2013, now U.S. Pat. No. 9,320,307, which is a continuation of and claims priority from U.S. patent application Ser. No. 12/815,019, filed Jun. 14, 2010, now U.S. Pat. No. 8,597,222, which claims priority from U.S. provisional patent application No. 61/186,500, filed Jun. 12, 2009; the contents of each of the foregoing patent applications are incorporated herein by reference in their entirety.

FIELD

This application relates to the field of athletic garments and other apparel and particularly to compression garments.

BACKGROUND

Compression garments are comprised of a stretchable material that generally adheres tightly to an individual in one or more areas of the body. Different compression garments are designed to provide different degrees of compression to a body part. However, the degree of compression provided by a given garment is dependent on the wearer's individual body shape and size. For example, two different athletes wearing a size large compression short may have significantly different thigh circumferences, resulting in significantly different amounts of compression provided by the garment. Furthermore, different individuals may prefer greater or lesser compression on a body part based on their own personal preferences, needs, activities and/or comfort levels.

Garments do not typically include a way for a wearer to tailor a compression garment to his or her individual needs or desires. Thus, for a particular individual, compression garments typically provide only one compression force, which provides a degree of compression based on the size of the individual. Therefore, it would be desirable to provide an adjustable compression garment that may be quickly and easily tailored to each individual consumer's particular needs.

SUMMARY

A garment configured to be worn on a human body is disclosed herein. In at least one embodiment, the garment is a short that includes at least one fabric portion and a compression adjustment arrangement. The least one fabric portion is comprised of an elastic material and is configured to provide a degree of compression to a human body part depending on a degree of stretch of the at least one fabric portion. The at least one fabric portion extends from a hip portion to a limb portion of the short. The compression adjustment arrangement is coupled to the at least one fabric portion. The compression adjustment arrangement includes a first lacing guide, a second lacing guide and a dial. Rotation of the dial is configured to move the first lacing guide toward the second lacing guide and increase an amount of compression provided by the elastic material.

In at least one embodiment, the garment comprises a first panel with a first lacing guide coupled to the first panel and a second panel with a second lacing guide coupled to the second panel. At least one of the first panel and the second panel is comprised of an elastic material. A cord extends between the first lacing guide and the second lacing guide. A cord adjustment mechanism is coupled to the cord. The cord adjustment mechanism is configured to reduce an effective length of the cord extending between the first lacing guide and the second lacing guide and move the first panel closer to the second panel.

In at least one additional embodiment, the garment comprises at least one elastic panel with a first lacing guide and a second lacing guide coupled to the at least one elastic panel. A non-elastic panel is provided between the first lacing guide and the second lacing guide. A cord extends between the first lacing guide and the second lacing guide and across the non-elastic panel. A cord adjustment mechanism is coupled to the cord. The cord adjustment mechanism is configured to reduce an effective length of the cord extending between the first lacing guide and the second lacing guide and move the first lacing guide closer to the second lacing guide.

In at least one further embodiment, a garment includes a torso portion and a leg extending from the torso portion. The leg includes at least one elastic panel, a first lacing guide, and a second lacing guide. A cord extends between the first lacing guide and the second lacing guide. A dial is positioned on the leg and coupled to the cord. The dial is configured to increase an amount of compression provided by the elastic panel by reducing an effective length of the cord extending between the first lacing guide and the second lacing guide and moving the first lacing guide closer to the second lacing guide.

The above described features and advantages, as well as others, will become more readily apparent to those of ordinary skill in the art by reference to the following detailed description and accompanying drawings. While it would be desirable to provide a garment with adjustable compression that provides one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

FIG. 1C shows an interior view of the thigh flap with the fastening arrangement of FIG. 1B provided in the form of a hook pad of a unidirectional hook arrangement;

FIG. 2A shows a side view of the hook pad of FIG. 1C;

FIG. 2B shows a diagrammatic side view of the unidirectional hook arrangement of FIG. 1C with the hook pad released from a loop pad;

FIG. 2C shows a diagrammatic side view of an alternative embodiment of the unidirectional hook and loop arrangement of FIG. 1C with dual hook pads released from one another;

FIG. 3A shows a diagrammatic side view of an angled fiber connection arrangement provided as an alternative embodiment of the unidirectional hook and loop arrangement of FIG. 2B;

FIG. 3B shows a front perspective view of a short including the angled fiber connection arrangement of FIG. 3A;

DESCRIPTION

Figure 1A:
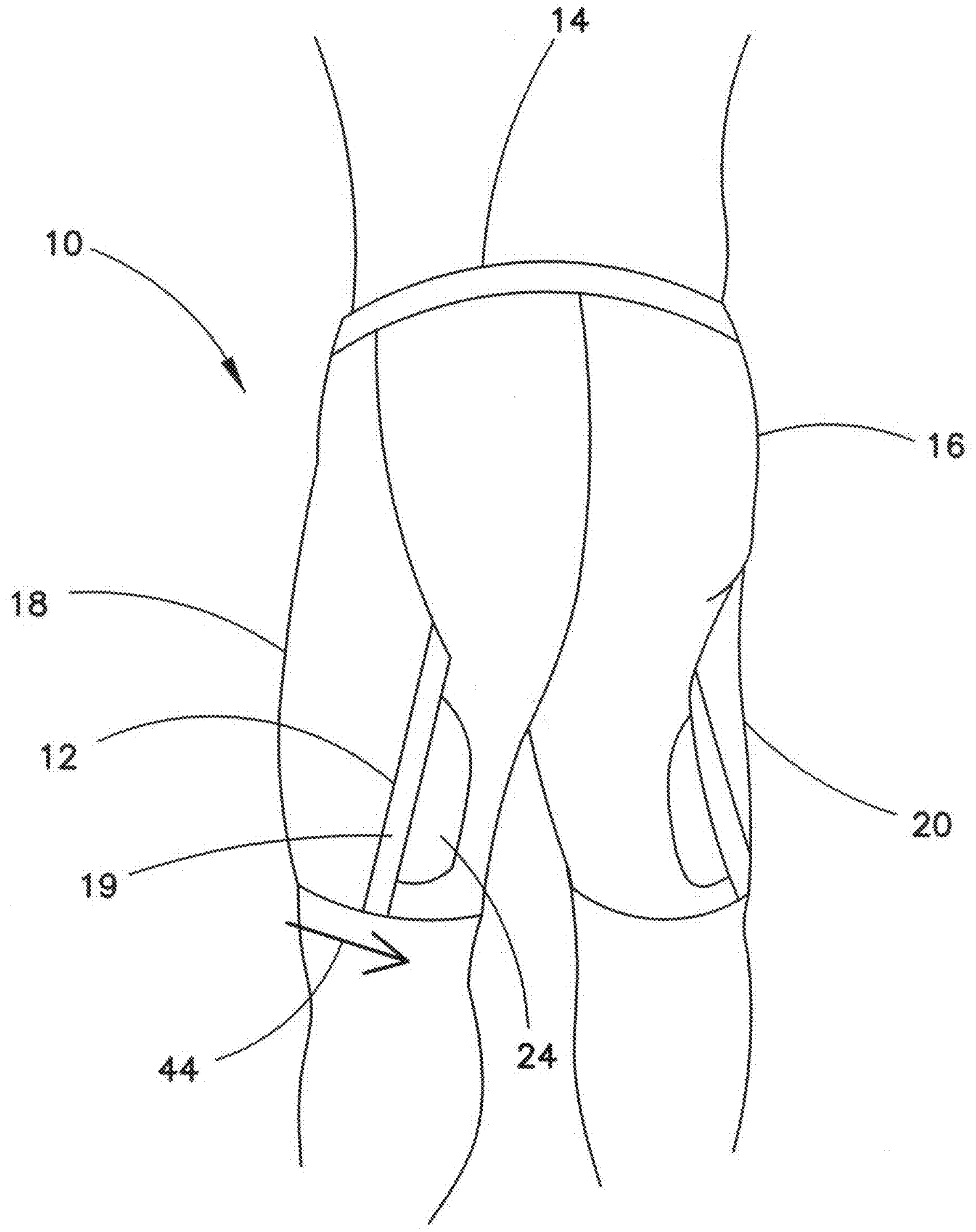
FIG. 1A shows a rear perspective view of an adjustable compression garment in the form of shorts providing adjustable compression.
Figure 1B:
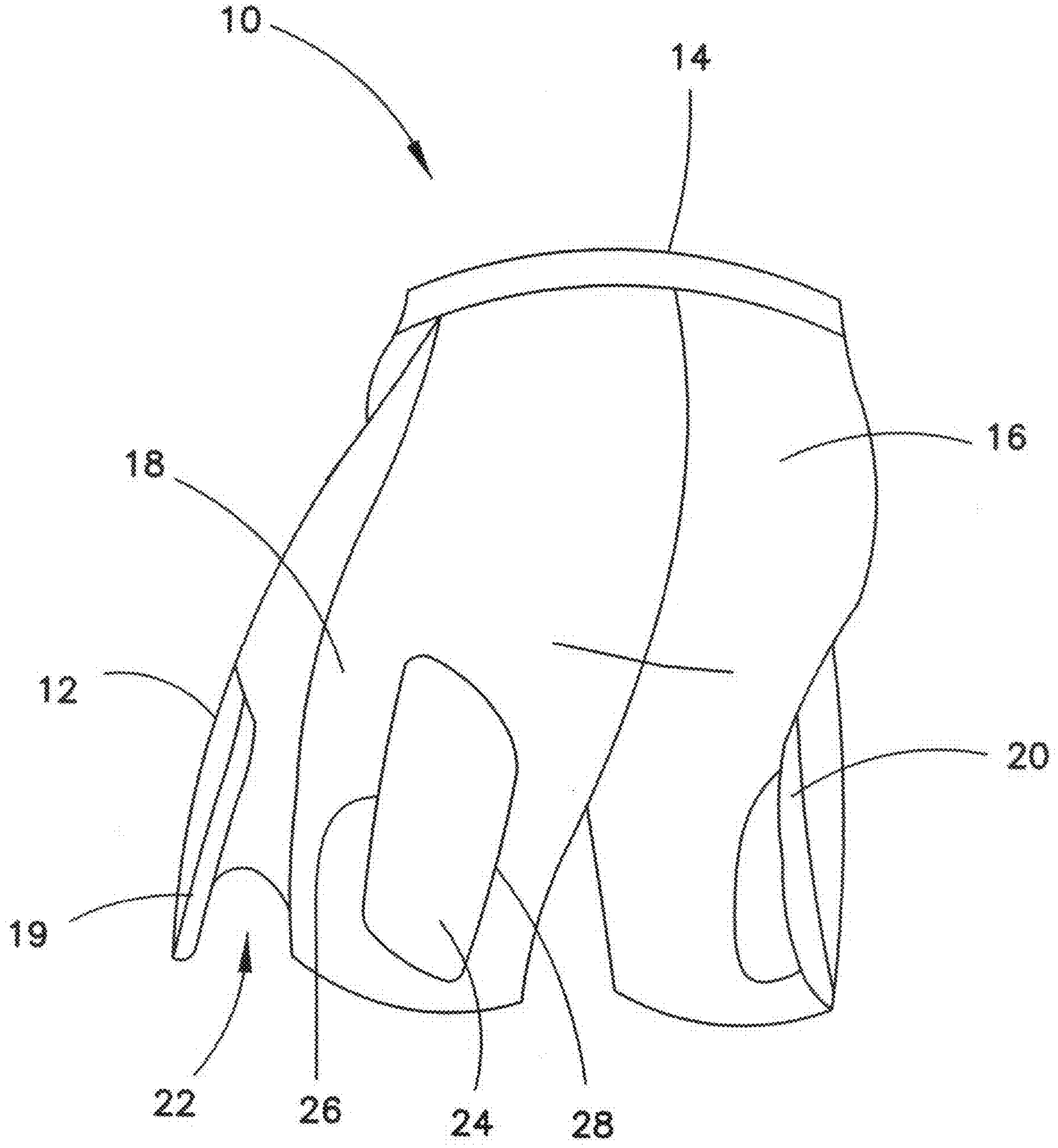
FIG. 1B shows the shorts of FIG. 1A with a thigh flap on the front portion of the shorts released from the rear portion of the shorts with a fastening arrangement included on the shorts.

With reference to FIGS. 1A-1C, a first embodiment of a garment with adjustable compression is shown in the form of a compression short 10 with an adjustable thigh flap 12. A compression adjustment arrangement is provided by a unidirectional hook and loop fastener arrangement that allows the thigh flap 12 to be adjusted on the short between a plurality of different positions. Each of the plurality of different positions stretches the fabric of the short to a different degree such that a different degree of compression is provided to the thigh of the individual wearing the short at each of the different positions.

The short 10 is generally comprised of a stretchable compression material such as a fabric including elastane, polyester, nylon, mixtures thereof, or other stretch fabrics (which may also be referred to herein as "elastic" materials or fabrics). However, it will be recognized that any fabric with some modulus of elasticity may be utilized in various embodiments of the garment with adjustable compression disclosed herein. Furthermore, although exemplary embodiments of the garment with adjustable compression are described herein with reference to a pair of short pants, it will be recognized that the garment may be provided in any of various other forms in other embodiments, such as shirts, arm sleeves, leg sleeves, socks, long pants, headgear, or any other type of garment.

In the embodiment of FIGS. 1A-1C, the short 10 generally comprises a torso portion and leg portions. The torso portion in the embodiment of FIGS. 1A-1C includes a waistband 14 and a pelvis portion 16. The limb portions include a left leg portion 18 and a right leg portion 20. The right leg portion 20 is substantially the same as the left leg portion 18, with the two leg portions 18 and 20 being substantially symmetric. Accordingly, only the left leg portion 18 will be described herein.

As shown in FIG. 1B, a slit 22 is formed in the left leg portion 18 with the thigh flap 12 provided along an edge of the slit 22. The slit 22 extends from the bottom of the left leg portion 18 to an area on the pelvis portion 16 near the waistband 14. The thigh flap 12 formed along the slit 22 is comprised of one portion of fabric that overlaps another portion of fabric on the short 10. A patch 19 may be provided along the edge of the thigh flap 12 to reinforce the thigh flap 12 and provide the wearer with an area to grasp when adjusting the thigh flap 12. While the slit 22 is shown in the embodiment of FIGS. 1A-1C as being provided along a lateral side of the leg portion 18, in other embodiments the slit 22 may be positioned in different places on the short, such as on a front or rear portion of the leg. Also, in other embodiments, the slit 22 may extend the substantial length of the short 10, as shown in FIG. 1B, or may extend a shorter distance along the leg portions 18 or 20.

Two complimentary fastener pads, leg pad 24 and flap pad 30 are provided on the left leg portion 18 of the short 10. The fastener pads 24 and 30 provide a fastener arrangement between the two portions of fabric separated by the slit 22. The fastener pads 24 and 30 are designed to releasably engage one another by any of various means, such as a hook and loop arrangement. The fastener pads include a leg pad 24 that is provided on an exterior hamstring area of the left leg portion 18. The leg pad 24 includes a lateral edge 26 and a rear edge 28 and is configured to engage a flap pad 30 (see FIG. 1C) provided on the interior portion of the thigh flap 12. The leg pad 24 is configured to engage the flap pad 30 at numerous locations between the lateral edge 26 and rear edge 28 and hold the flap pad 30 in place against the leg pad 24. When the leg pad 24 engages the flap pad 30, the slit 22 is closed in the shorts 10 and the compression fabric is stretched to some degree around the leg of the wearer. Therefore, the leg pad 24 and the flap pad 30 provide a compression adjustment arrangement capable of varying a degree of compression provided to the leg portion 18 of the wearer based on the engagement position of the flap pad 30 relative to the leg pad 24. A lesser degree of compression is provided on the leg of an individual wearing the short when the thigh flap 12 and associated flap pad 30 are positioned closer to the lateral edge 26 of the leg pad 24. A greater degree of compression is provided on the leg of an individual wearing the short when the thigh flap 12 and associated flap pad 30 are positioned closer to the rear edge 28 of the leg pad 24. The reason for this is that the fabric encircling the leg portion 18 must be stretched to a greater extent when the flap pad 30 is joined toward the rear edge 28 of the leg pad 24, thus providing greater compression around the leg.

The materials used to provide the leg and flap pads 24 and 30 may be any of a number of different fastener materials. For example, in the embodiment of FIGS. 1A-1C, the leg and flap pads 24 and 30 are comprised of a unidirectional hook and loop fastener arrangement, with all of the loops provided on the leg pad 24 and all of the hooks provided on the flap pad 30.

An exemplary embodiment of the flap pad 30 providing the hooks 32 for a unidirectional hook and loop fastener arrangement is shown in FIGS. 2A-2B. As shown in FIG. 2A, with a unidirectional hook and loop fastener arrangement, all of the hooks 32 are oriented in the same direction instead of multiple different orientations as is typical with most hook and loop fasteners. An opening 34 for receiving loops is formed between the tip 36 of each hook 32 and the base portion 38 of the flap pad 30. Even though all of the hooks 32 are oriented in the same direction with the unidirectional hook and loop arrangement, all of the loops 42 on the leg pad 24 are generally not oriented in the same direction. With such a unidirectional hook and loop arrangement, when the leg pad 24 is engaged with the flap pad 30, the two pads easily slide across each other in a first direction (see arrow 44 in FIGS. 1 and 2B), but the two fastener pads 24 and 30 are locked in place when slid in an opposite direction (e.g., the direction opposite arrow 44 in FIGS. 1 and 2B). Furthermore, because the ends of the hooks 32 wrap around the loops 42, the two fastener pads 24 and 30 do not easily pull away from one another (e.g., in a direction perpendicular to arrow 44 in FIG. 2B).

With the unidirectional hook and loop arrangement described above, the fastener pads 24, 30 may be oriented on the shorts 10 to allow a wearer to easily adjust the compression provided on the wearer's thighs. In particular, fastener pads 24, 30 may be oriented such that the wearer may bring the thigh flap 12 and associated flap pad 30 into engagement with the leg pad 24 near the lateral edge 26 of the first fastener and then slide the thigh flap 12 along the leg pad 24 (in the direction of arrow 44 of FIGS. 1 and 2B) in order to gradually increase the degree of compression. As the flap pad 30 slides over the leg pad 24, the rounded portion of the hooks 32 slides over the loops 42 without engaging the loops 42. When a desired level of compression is achieved, the wearer moves the thigh flap 12 slightly in the opposite direction, or simply releases the thigh flap 12, allowing the compression fabric to pull the thigh flap 12 in the opposite direction. This movement of the thigh flap 12 in the opposite direction causes the hooks 32 on the flap pad 30 to hook around the loops 42 on the leg pad 24. This locks the thigh flap 12 in place on the shorts 10 and also locks in the desired degree of compression. It will also be recognized that this arrangement provides for compression adjustment by sliding two components relative to one another along a planar level without the need to lift one component away from the other. This would not be possible if traditional hook and loop arrangements were used as the fastener pads 24 and 30, as traditional hook and loop arrangements would prohibit the sliding of the leg pad 24 relative to the flap pad 30. Accordingly, the compression adjustment arrangement is configured to (i) retain the compression fabric of the short 10 at a first degree of stretch, (ii) increase the degree of stretch of the at least one fabric portion from the first degree of stretch to a second degree of stretch without releasing the at least one fabric portion from the first degree of stretch to a lesser degree of stretch, and (iii) retain the at least one fabric portion at the second degree of stretch.

After sliding the flap pad 30 along the leg pad 24 to achieve a given level of compression, the user may wish to reduce the compression level. In order to accomplish such a reduction in the compression level, he or she simply slides the fastener pads 24 and 30 only slightly in the compression direction in order to release the hooks 32 from the loops 42. The wearer then pulls the thigh flap 12 and associated flap pad 30 outward and away from the leg pad 24, thus releasing the thigh flap 12 from the leg pad 30.

In at least one alternative embodiment of the arrangement shown in FIGS. 1A-2B, the hook and loop fastener arrangement may be substituted for a dual unidirectional hook arrangement, such as that shown in FIG. 2C. In such an embodiment, each of the fastener pads 24 and 30 includes a unidirectional hook arrangement. The pads 24 and 30 are arranged such that the hooks 33 on the leg pad 24 catch the hooks 32 on the opposing flap pad 30 when the flap pad 30 is moved relative to the leg pad 24 in the direction of arrow 45. When the hooks 32 and 33 catch each other, the fastener pads 24 and 30 are locked together and the flap pad 30 is prevented from further movement relative to the leg pad 24 in the direction of arrow 45. However, when the flap pad 30 is moved in the opposite direction from arrow 45, the curved portions of the hooks 32 on the flap pad 30 slide over the curved portions of the hooks 33 on the leg pad 24, allowing the flap pad 30 to move relative to the leg pad 24 in the direction opposite arrow 45. Accordingly, the molded unidirectional hook arrangement of FIG. 2A is advantageous in both of the embodiments of FIGS. 2B and 2C because it does not easily snag fabric in one direction of movement. Furthermore, particles are also not easily collected in the hooks since there is no double-sided hook to lock particles in the arrangement. As used herein, the term "unidirectional hook arrangement" refers to an arrangement where substantially all of the hooks of the fastener member are oriented in the same general direction, including a unidirectional hook and loop arrangement, such as that of FIG. 2B, and a dual unidirectional hook arrangement, such as that of FIG. 2C.

With reference now to FIGS. 3A-3D, another alternative embodiment of the short 10 with adjustable compression is shown. This embodiment is similar to that of FIGS. 1A-2B, but instead of a unidirectional hook and loop arrangement, the fastener arrangement is provided by fastener pads that comprise angled fibers (commonly referred to as a "cat's tongue" arrangement). In particular, the leg pad 24 includes a plurality of plush fibers 50 and the opposing flap pad 30 also includes a plurality of plush fibers 52. The fibers 50 and 52 are oriented approximately 45° relative to the respective substrates 51, 53 from which the fibers extend. The fibers 50, 52 may be comprised of any of numerous different materials, such as nylon or mohair, for example, or various other synthetic or natural fibers that may be attached to the substrates 51, 53 at an angle and resiliently maintained at such angle. In order to achieve this resilient orientation of the fibers a roller or other mechanism may be used to force the fibers 50, 52 downward while heat is simultaneously applied to the fibers, thus locking the orientation of the fibers relative to their respective substrates 51, 53.

Figure 3C:
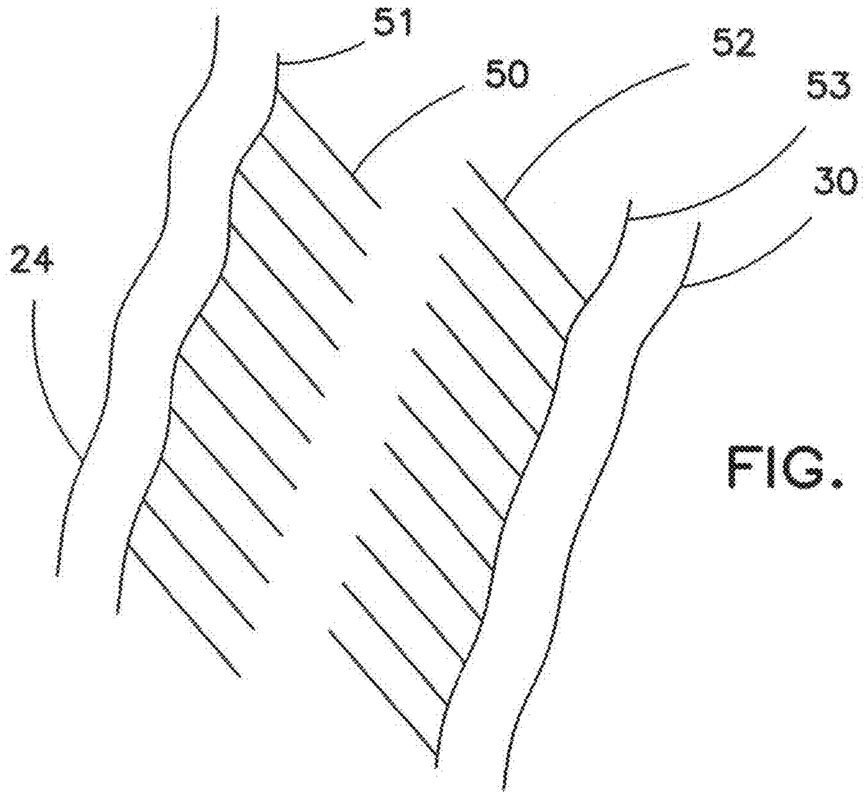
FIG. 3C shows an enlarged view of the fibers of the angled fiber connection arrangement of FIG. 3A with the fibers disengaged.
Figure 3D:
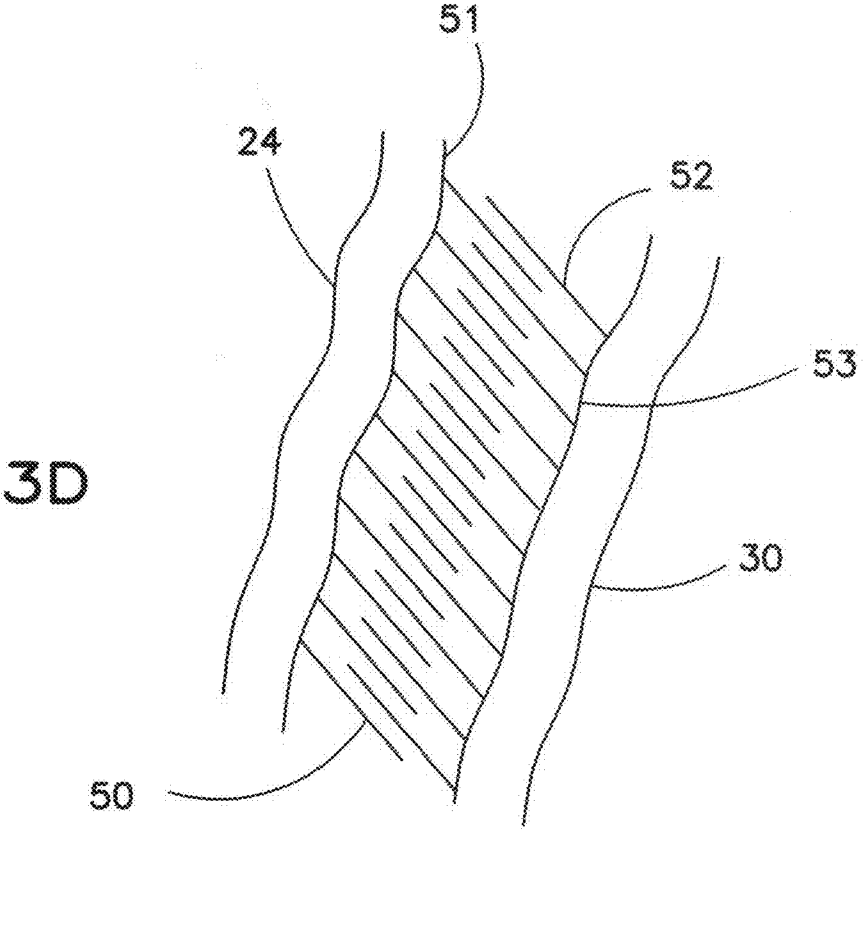
FIG. 3D shows an enlarged view of the fibers of the angled fiber connection arrangement of FIG. 3A with the fibers engaged.

When the leg pad 24 faces the flap pad 30, as shown in FIGS. 3A and 3C, the fibers 50, 52 on the respective pads 24, 30 point in opposite directions. If the flap pad 30 is brought into engagement with the leg pad 24, the fibers 50 and 52 mesh together, as shown in FIG. 3D. The orientation of the fibers allows the flap pad 30 to slide over the leg pad 24 in one direction (e.g. in the direction of arrow 54 shown in FIGS. 3A and 3B). However, the orientation of the fibers 50, 52 prevents the flap pad 30 from moving in an opposite direction relative to the leg pad 24 (i.e., a direction opposite arrow 54).

The fastener pads 24, 30 provide a compression adjustment arrangement for the shorts 10. Thus, the fastener pads 24, 30 are oriented on the shorts 10 to allow a wearer to easily adjust the compression provided on the wearer's thighs. In particular, pads 24, 30 may be oriented such that the wearer may bring the thigh flap 12 and associated flap pad 30 into engagement with the leg pad 24 near the lateral edge 26 of the leg pad 24 and then slide the thigh flap 12 and associated flap pad 30 along the leg pad 24 (in the direction of arrow 54 of FIGS. 3A and 3B) in order to gradually increase the degree of compression. This gradual increase in the degree of compression may be accomplished without decoupling the leg pad 24 from the flap pad 30. As the flap pad 30 slides over the leg pad 24, the plush fibers 52 of the flap pad 30 slide over the plush fibers 50 of the leg pad 24. When a desired level of compression is achieved, the wearer releases the thigh flap 12, allowing the compression fabric to pull the thigh flap 12 in the opposite direction, and causing the plush fibers to mesh together in a locking arrangement as shown in FIG. 3D. This locks the thigh flap 12 in place on the shorts 10 and also locks in the desired degree of compression. Similar to the embodiment of FIGS. 1A-2B, this arrangement provides for compression adjustment by sliding two components relative to one another along a planar level without the need to lift one component away from the other or disconnect the two components. Also, the compression adjustment arrangement is configured to (i) retain the compression fabric at a first degree of stretch, (ii) increase the degree of stretch of the at least one fabric portion from the first degree of stretch to a second degree of stretch without releasing the at least one fabric portion from the first degree of stretch to a lesser degree of stretch, and (iii) retain the at least one fabric portion at the second degree of stretch.

As shown in FIG. 3B, a flap 56 is attached to the left leg portion 18 and extends over the thigh flap 12 in order to block the thigh flap 12 from moving outward and away from the leg pad 24. The flap 56 is provided by a swath of fabric that is secured to the pelvis portion 16 of the shorts, extends over the flap pad 30, and is releasably attached to the bottom of the left leg portion 18. Accordingly, the flap 56 may include a hook and loop type fastener on an interior of the end portion of the flap 56 that engages a complimentary fastener near the exterior hem of the leg portion 18. When the fastener on the flap 56 is removed from the fastener on the leg portion, the flap 56 may be peeled away to expose the thigh flap 12. This allows the wearer to then release the thigh flap 12 from the leg pad 24 by simply pulling the thigh flap 12 outward and away from the leg pad 24. In at least one alternative embodiment, the flap 56 may be comprised of a stretch fabric that is fixed to both the pelvis portion 16 of the shorts 10 and the hem of the left leg portion 18. In this embodiment, the wearer may gain access to the thigh flap 12 by pulling the flap 56 outward and away from the thigh flap 12, thus stretching the flap 56 and allowing the user to manipulate the thigh flap 12 as desired.

Figure 4A:
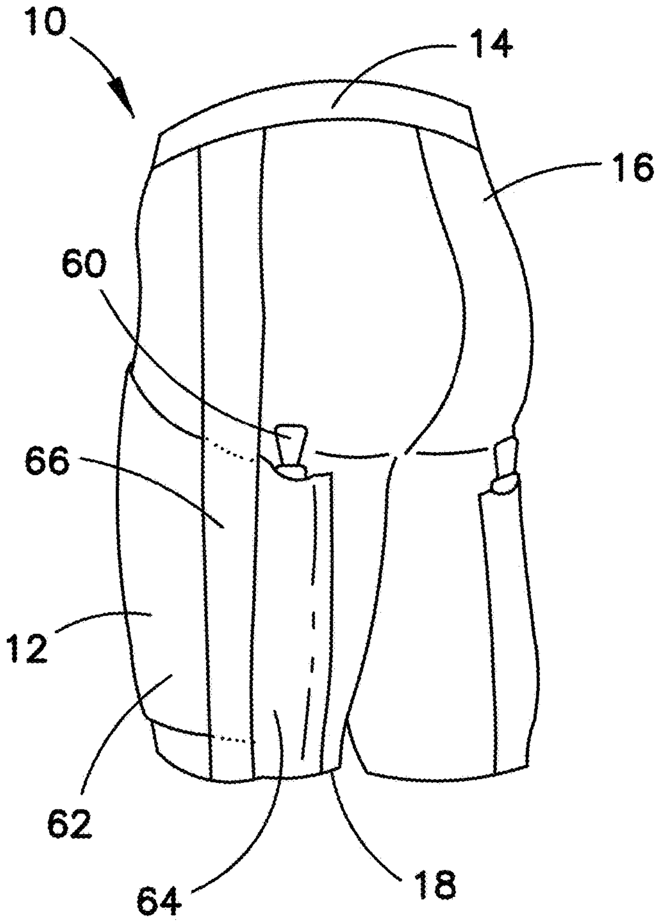
FIG. 4A shows a rear perspective view of an alternative embodiment of the adjustable compression short of FIG. 1A using a roller bar and pocket as a fastening arrangement.
Figure 4B:
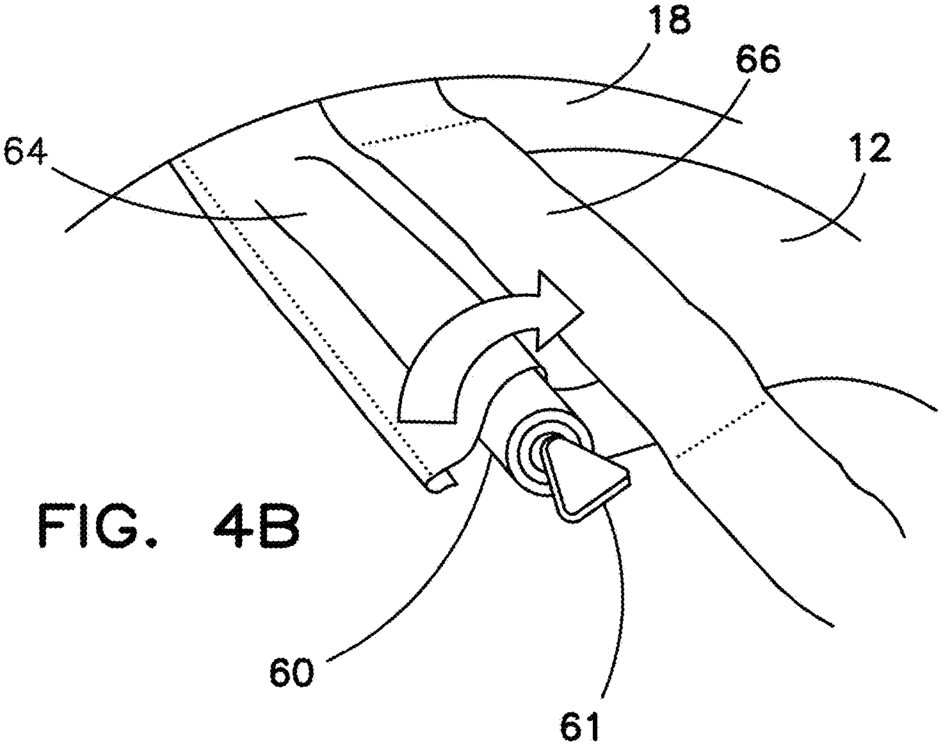
FIG. 4B shows an upper rear perspective view of the fastening arrangement of FIG. 4A.

With reference now to FIGS. 4A and 4B, in an alternative embodiment of the shorts 10 with adjustable compression, the thigh flap 12 is provided as an elongated swath of fabric 62 (or "power strip") that engages a roll bar 60. The roll bar 60 provides a fastener arrangement that couples the elongated swatch of fabric 62 to the back side of the shorts 10. The roll bar 60 includes a stationary outer portion and a rotatable inner bar portion. The rotatable inner bar is coupled to the power strip 62. The roll bar 60 is configured such that the inner bar may be rotated in a manner that rolls the end portions of the power strip 62 into the roll bar 60 or allow the end portions of the power strip 62 to be released from the roll bar 60. The outer portion roll bar 60 is fixedly retained within a sleeve 64 on the left leg portion 18 of the shorts 10. The sleeve 64 may be provided by a stretch material, similar to the compression fabric of the shorts 10, or may be provided by other material. A knob 61 is provided at the top of the roll bar 60 and is connected to the rotatable inner bar. The knob 61 allows a user to rotate the roll bar 60 such that the roll bar 60 provides a compression adjustment arrangement for the shorts 10. When the knob 61 is rotated in one direction, the roll bar 60 pulls fabric around the roll bar 60, thus stretching the fabric on the power strip 62 pulling on the power strip 62 and increasing the compression around the wearer's thigh. Accordingly, the roll bar 60 may include a locking component that allows the roll bar 60 to be locked in place to achieve a desired compression. When the knob 61 is rotated in an opposite direction, fabric on the power strip 62 is released from the roll bar 60, thus decreasing the compression around the wearer's thigh. A tensioner 66 covers the power strip 62 next to the sleeve 64. The tensioner 66 may be comprised of a swath of fabric that is connected to the left leg portion 18 and the pelvis portion 16 or other upper portion of the leg portion 18. The power strip 62 extends under the tensioner 66 and the tensioner 66 maintains the power strip 62 in a close engagement against the leg portion 18. Similar to the embodiments of FIGS. 1A-3B, the embodiment of FIGS. 4A and 4B provides for compression adjustment on a garment by sliding two components relative to one another along a planar level without the need to lift one component away from the other or disconnect the two components. Of course, in the embodiment of FIGS. 4A and 4B, the sliding is accomplished with the assistance of a mechanical device in the form of the roll bar 60. Moreover, the compression adjustment arrangement of FIGS. 4A and 4B is also configured to (i) retain the compression fabric of the shorts 10 at a first degree of stretch, (ii) increase the degree of stretch of the at least one fabric portion from the first degree of stretch to a second degree of stretch without releasing the at least one fabric portion from the first degree of stretch to a lesser degree of stretch, and (iii) retain the at least one fabric portion at the second degree of stretch.

Figure 5:
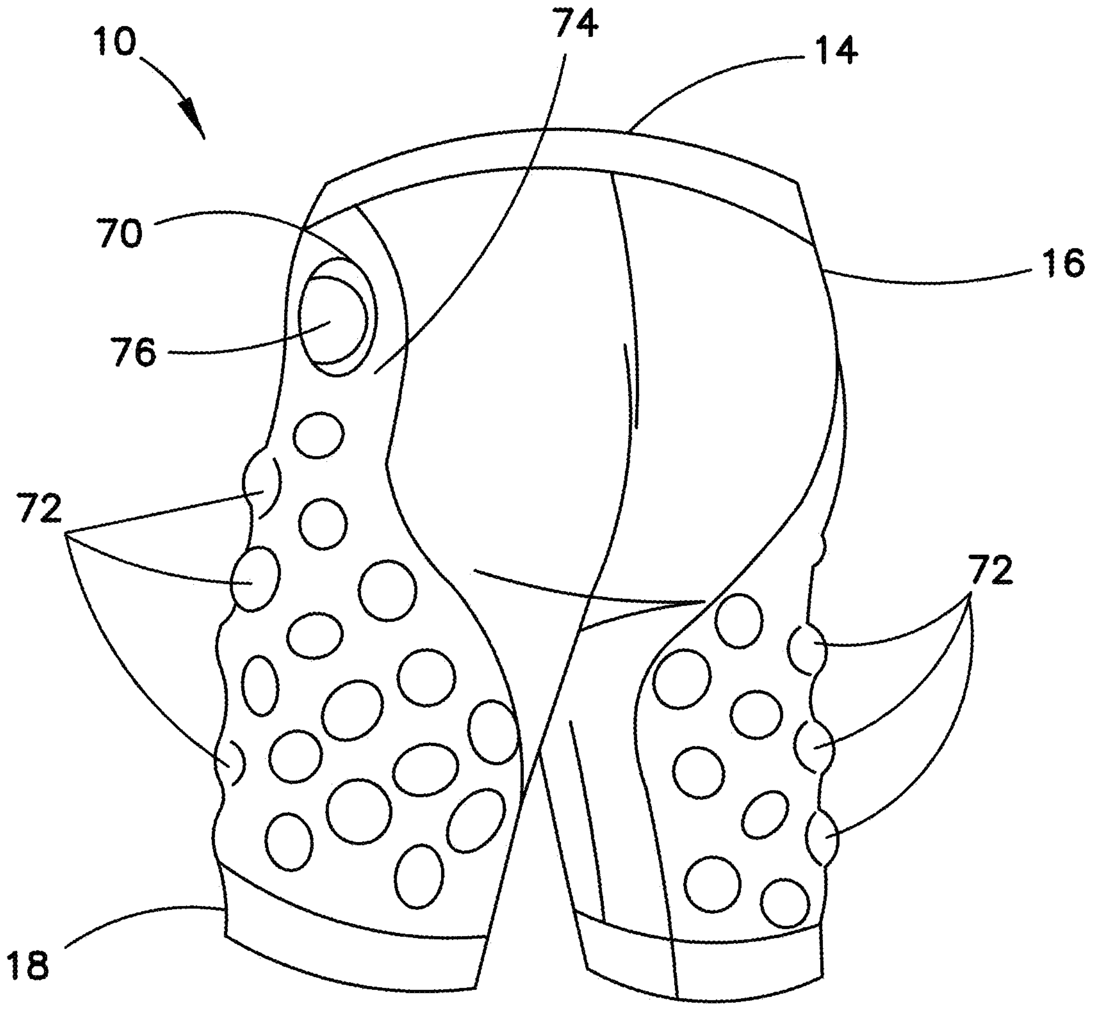
FIG. 5 shows a rear perspective view of an alternative embodiment of the adjustable compression short of FIG. 1A using a pump and air pockets to adjust the degree of compression.

With reference now to FIG. 5, an alternative embodiment of the short 10 with adjustable compression is provided in the form of a short 10 including a pump 70 for moving fluid, e.g., air, with a plurality of inflatable pockets 72 that provide the compression adjustment arrangement. The pump 70 is in fluid communication with the pockets 72 which are provided within or on a compression panel 74 that covers a substantial part of the left leg portion 18. The compression panel 74 may also extend to other portions of the short, such as the pelvis portion 16, as shown in FIG. 5. The compression panel 74 is comprised of a compression fabric that includes elastane or any of various other stretch materials. The compression panel 74 may cover other compression fabric provided on the left leg portion 18, such that the pockets 72 are positioned between an inner layer of compression fabric and an outer layer of compression fabric provided by the compression panel 74.

The pump 70 is a hand operated push pump. The pump includes a flexible diaphragm 76 that covers a fluid cavity behind the flexible diaphragm 76. The fluid cavity is inconnected to the network of pockets 72. The pockets 72 are all interconnected by channels (not shown) that extend between the pockets 72. The pockets 72 and interconnecting channels may be encased with a flexible plastic material that allows the pockets and channels to expand and contract as fluid moves in and out of the pockets and channels.

When a user presses on the flexible diaphragm 76, fluid in the cavity behind the diaphragm 76 is forced out from the cavity and into the network of pockets 72. When the user releases the diaphragm 76, the resilient diaphragm returns to an outward position and draws additional fluid into the cavity. A one-way valve (not shown) provided between the cavity and the network of air pockets 72 prevents fluid from escaping from the network of air pockets 72 when the diaphragm 76 is released. With each subsequent depression of the diaphragm additional fluid is forced into the network of air pockets 72. As the pockets 72 fill with fluid, they expand and cause the compression fabric around them to stretch. This, in turn, increases the compression provided by the compression fabric of the shorts 10. The wearer may continue to depress and release the diaphragm 76 until the desired level of compression is achieved. When the wearer wishes to decrease the compression level, the user activates a relief valve (not shown) which allows fluid to escape from the network of pockets 72. In view of the foregoing description, it will be recognized that the compression adjustment arrangement of FIG. 5 is therefore configured to (i) retain the compression fabric of the shorts 10 at a first degree of stretch, (ii) increase the degree of stretch of the at least one fabric portion from the first degree of stretch to a second degree of stretch without releasing the at least one fabric portion from the first degree of stretch to a lesser degree of stretch, and (iii) retain the at least one fabric portion at the second degree of stretch.

With reference now to FIGS. 6A-6E, an alternative embodiment of an adjustable compression garment is shown as a short 10 with an adjustable lacing system 80 as the compression adjustment arrangement. Each leg of the short 10 includes a front panel 82 and a rear panel 84 with a side panel 86 positioned in between the front panel 82 and the rear panel 84. The short 10 includes a fastening arrangement comprised of a plurality of lacing guides 88, a cord 90, and a cord adjustment mechanism 100. The lacing guides 88 are connected to the front panel 82 and the rear panel 84 at positions near the side panel 86. The lacing guides 88 may be provided in any of various forms, as will be recognized by those of ordinary skill in the art, including "eyestays" or "eyelets". The cord 90 is threaded between the plurality of lacing guides 88 such that the lacing guides 88 are connected to one another by the cord 90. The cord 90 is also connected to a cord adjustment mechanism 100 which is configured to reduce and elongate the effective length of the cord 90 that extends between the plurality of lacing eyestays 88. As used herein, the term "cord" refers to lacing used in a lacing arrangement. The cord may be provided in any of various forms as will be recognized by those of ordinary skill in the art, such as a braided or woven rope, cable or other elongated strip of material.

The front panel 82 and rear panel 84 of the short 10 are comprised of a compression fabric, such as, for example, an elastane or other stretch fabric. The side panel 86 is comprised of a relatively inelastic material, such as a synthetic leather material. In at least one embodiment, a mesh backer 87 (see FIG. 6B) may be provided on the inside of the side panel 86 to provide additional comfort for the wearer, and separate the side panel 86 from the wearer's skin.

Figure 6A:
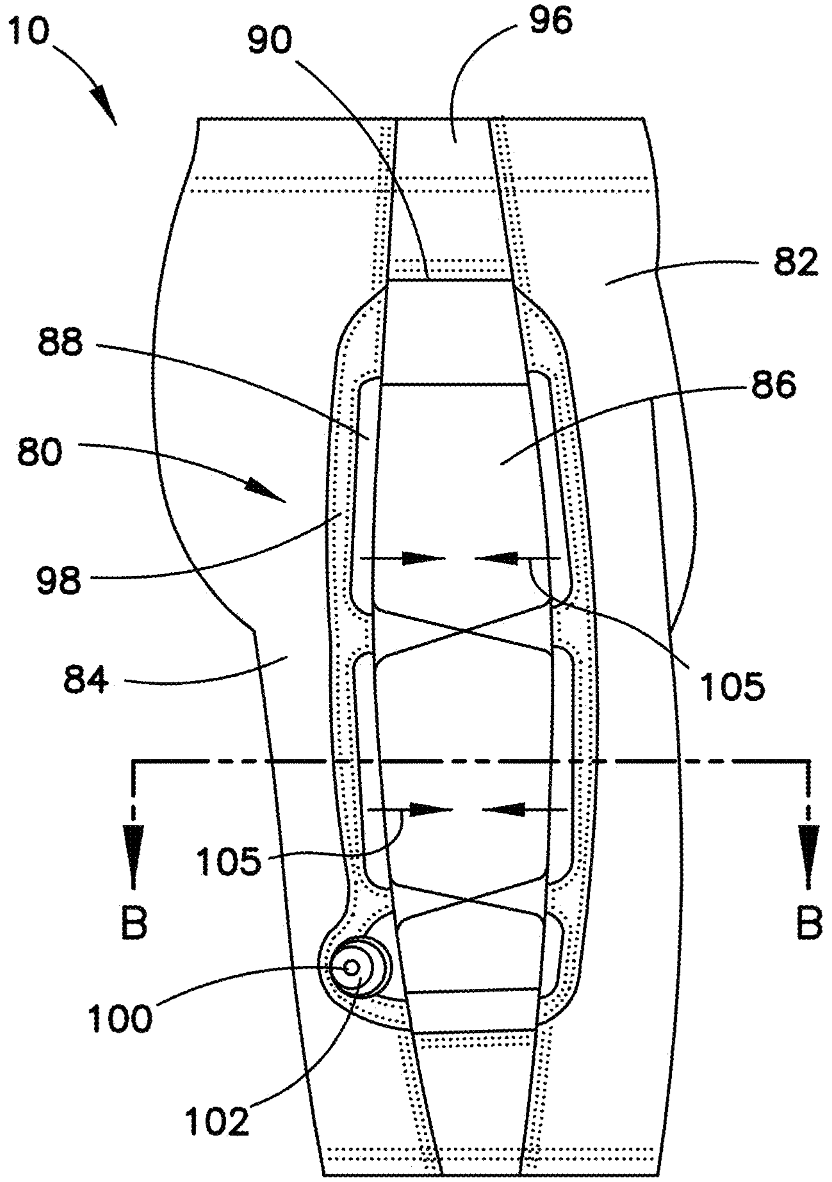
FIG. 6A shows a side view of an alternative embodiment of the adjustable compression short of FIG. 1A with a lacing system as the fastening arrangement.
Figure 6B:
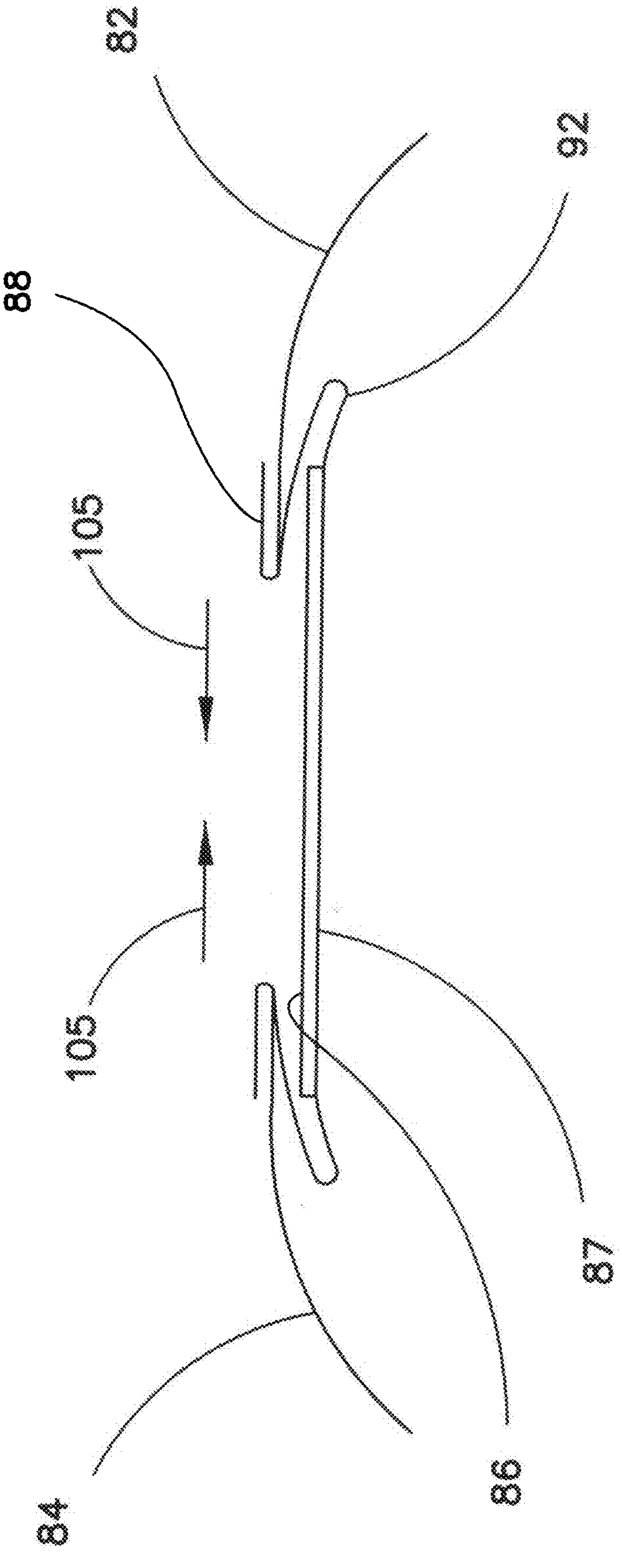
FIG. 6B shows a cross-sectional view of the adjustable compression short along line B-B of FIG. 6A.
Figure 6C:
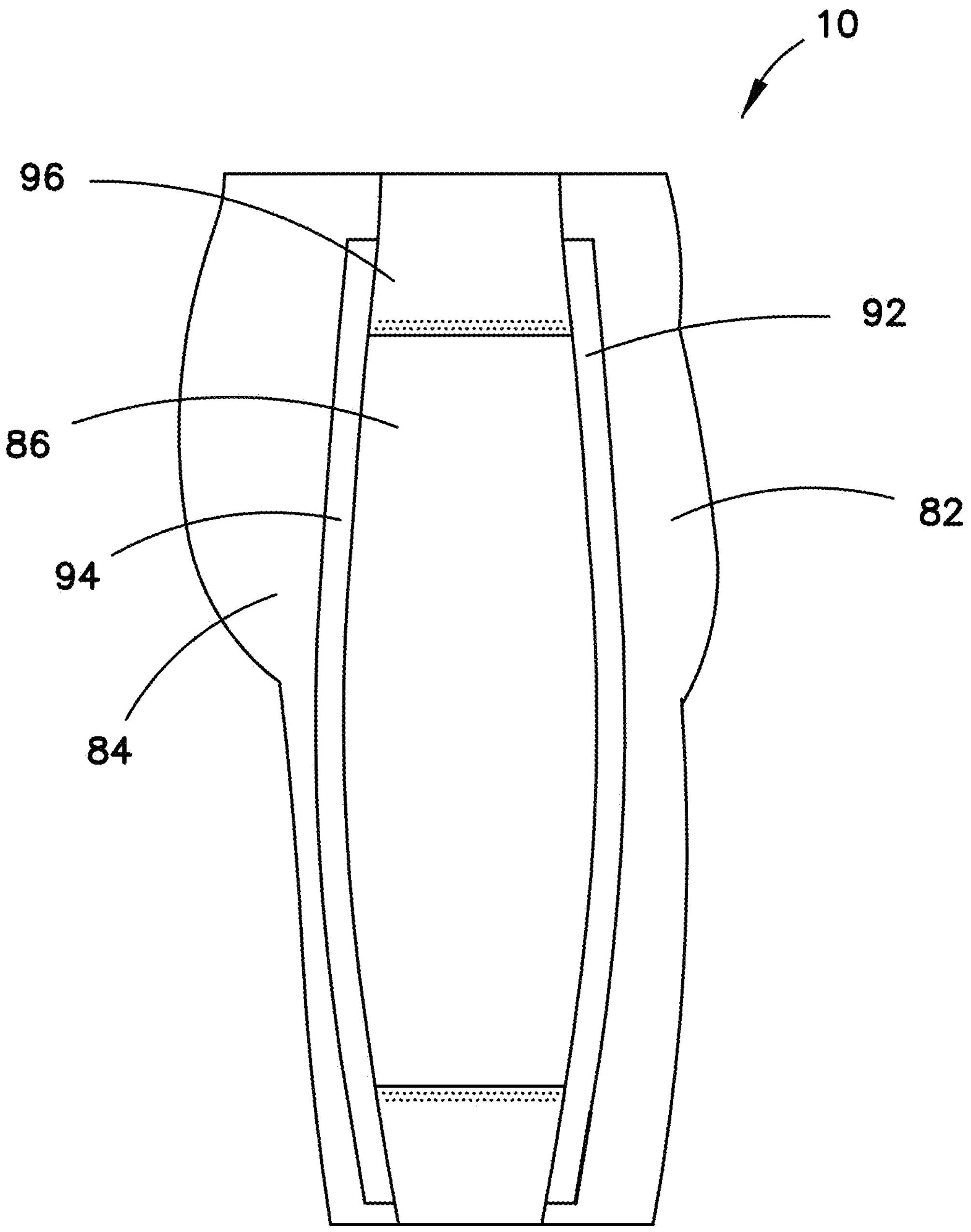
FIG. 6C shows an interior side view of the adjustable compression short of FIG. 6A.
Figure 6D:
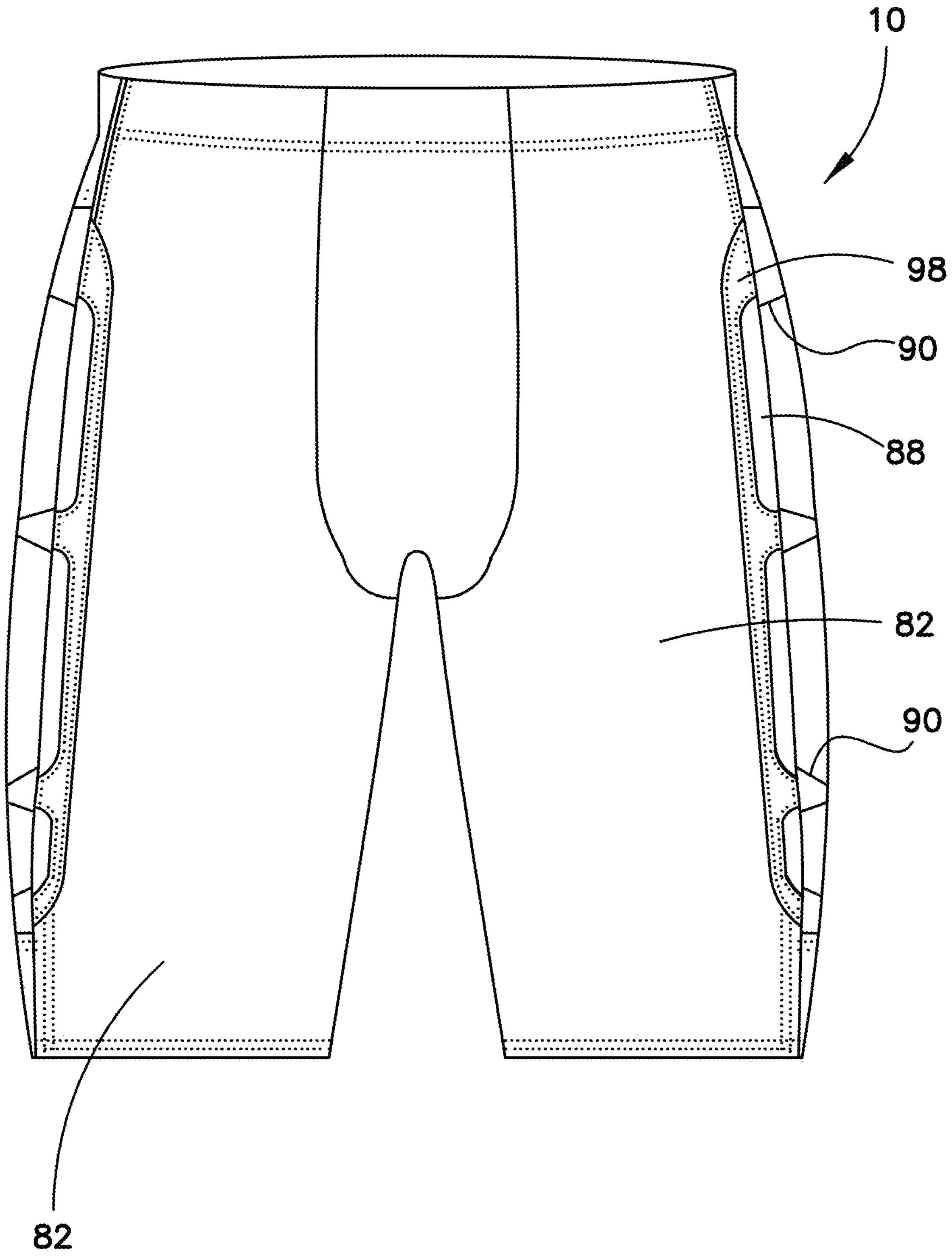
FIG. 6D shows a front view of the adjustable compression short of FIG. 6A.
Figure 6E:
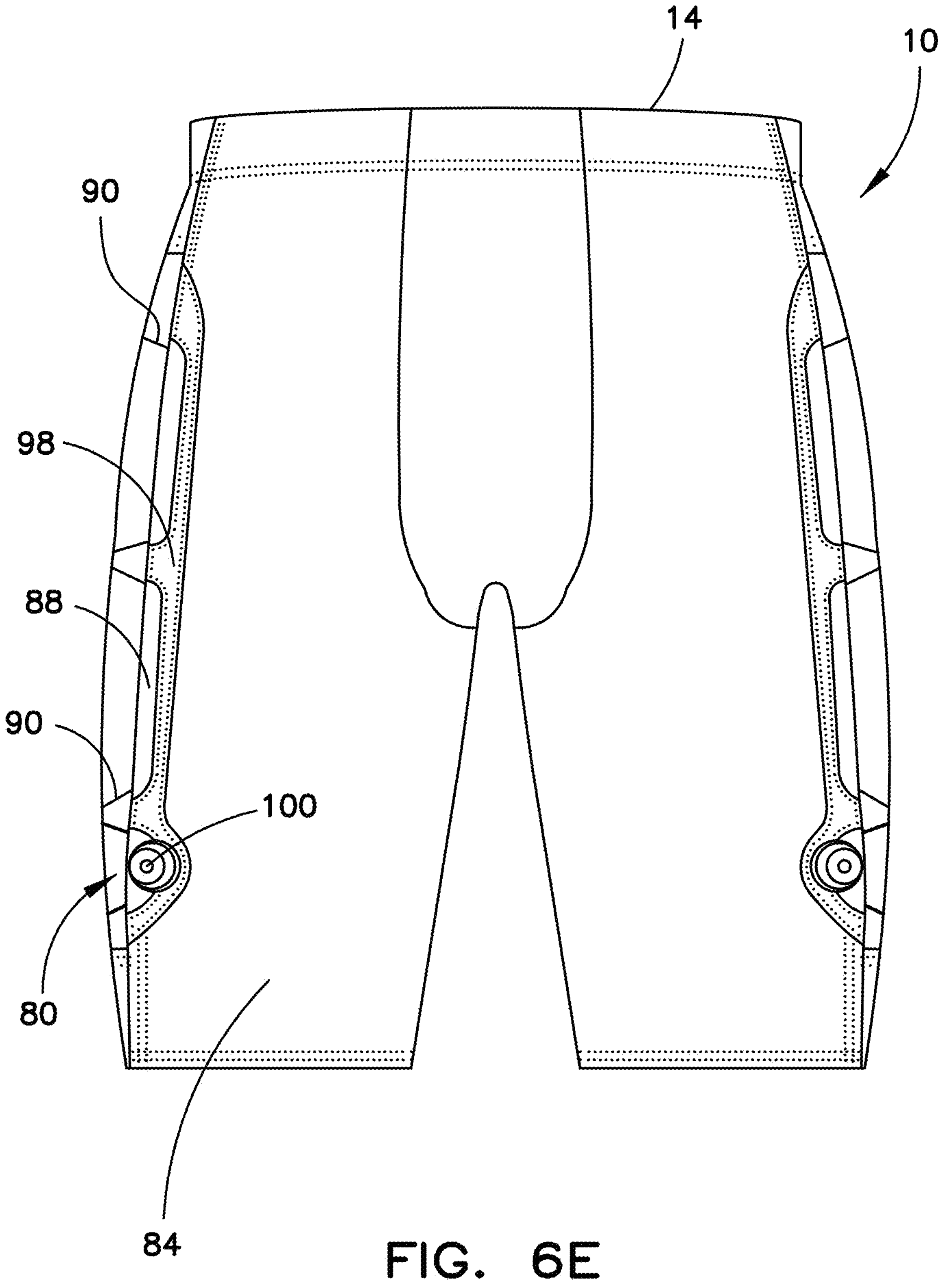
FIG. 6E shows a rear view of the adjustable compression short of FIG. 6A.

As shown in FIGS. 6B and 6C, a fold-over gusset 92 connects the front panel 82 to one side of the side panel 86. Another fold over gusset 94 connects the rear panel 84 to the opposite side of the side panel 86. In at least one embodiment, the fold-over gussets 92, 94 may also be comprised of a compression fabric. However, in other embodiments, the fold-over gussets 92, 94 may be comprised of other materials, including relatively inelastic materials, such as synthetic leather.

As shown in FIGS. 6A and 6C, a side extension panel 96 connects the front panel 82 to the rear panel 84 near the top of the short 10 and the bottom of the short. This side extension panel 96 may be comprised of any type of fabric, including compression fabrics and relatively inelastic fabrics. As also shown in FIG. 6A, a reinforcement overlay 98 may also be used to stabilize the area where the lacing eyestays 88 are connected on the short 10. The reinforcement overlay 98 is typically comprised of a relatively strong and relatively inelastic material, such as a synthetic leather. However, in other embodiments the reinforcement overlay 98 may also be comprised of any of numerous other fabrics, including compression fabrics.

Figure 7A:
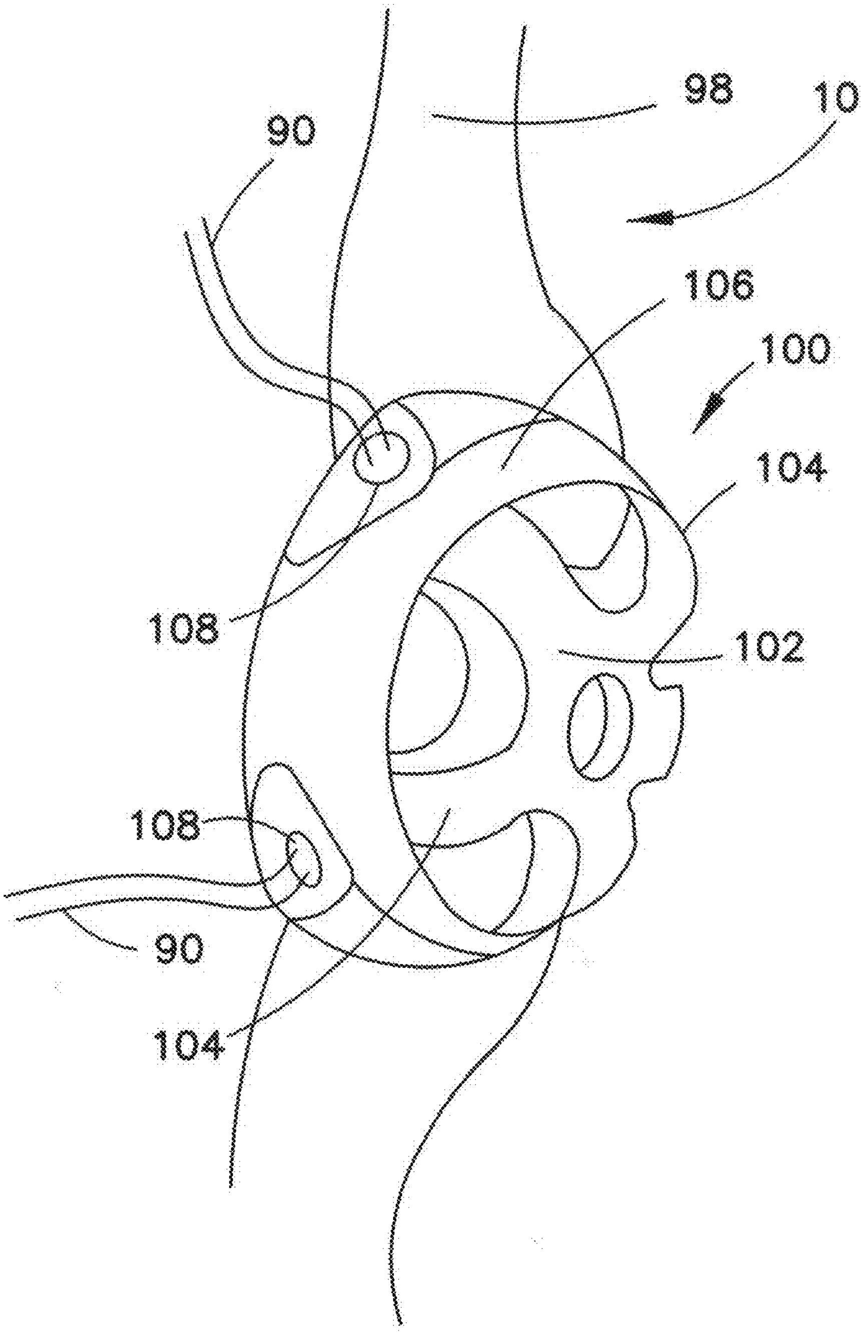
FIG. 7A shows a cord adjustment mechanism configured for use with the lacing system of the adjustable compression shorts of FIG. 6A.
Figure 7B:
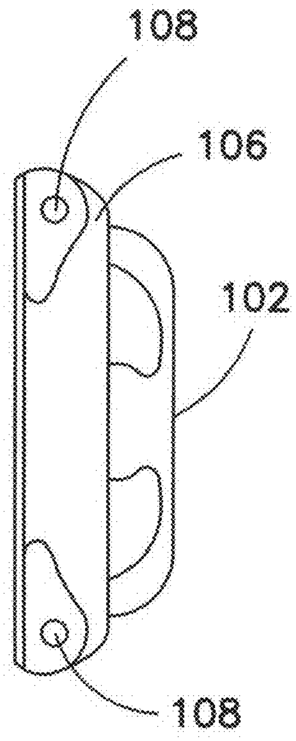
FIG. 7B shows a side view of the cord adjustment mechanism of FIG. 7B.

The cord adjustment mechanism 100 for the embodiment of FIGS. 6A-6E is provided as a rotatable dial and spool arrangement. An exemplary rotatable dial and spool arrangement is shown in FIGS. 7A and 7B. In this embodiment, the dial 102 is configured for rotation by a human hand. Accordingly, the dial 102 includes a plurality of ribs 104 designed and dimensioned to engage the fingers of the wearer, thus allowing the wearer to rotate the dial 102. The dial 102 is retained within a generally circular base portion 106. The base portion 106 includes two openings 108 that receive the cord 90, and allow the cord 90 to move into and out of the cord adjustment mechanism 100 when a spool (not shown) of the cord adjustment mechanism 100 is rotated. The spool is connected to the dial 102 and is made to rotate when the dial 102 is rotated.

In operation, when the wearer rotates the dial 102 in one direction, the spool connected to the dial 102 reels in a length of the cord 90, thus reducing the effective length of the cord that is threaded between the lacing eyestays 88. When the effective length of the cord 90 is reduced, the eyestays 88 are drawn together, as represented by arrows 105 in FIGS. 6A and 6B. A ratchet mechanism (not shown) connected to the spool prevents the length of cord reeled into the spool from being released from the spool. When the eyestays 88 are drawn together, the front panel 82 and rear panel 84 are stretched in the direction of arrows 105, thus increasing the degree of compression on a wearer's thighs. If the wearer wishes to relieve the compression, he or she presses a release button (e.g., depresses the dial 102 or another button on the base portion 106) in order to release the spool from the ratchet mechanism. When the spool is released from the ratchet mechanism, the spool is unlocked and free to rotate in an opposite direction that allows the cord 90 to be pulled away from the spool. With the cord unlocked, the eyestays 88 pull away from each other in a direction opposite the direction shown by arrows 105, thus pulling the cord 90 from the spool and releasing the degree of compression provided by the shorts 10. Accordingly, the wearer is provided with a garment having an adjustable compression arrangement where the adjustable compression panels remain connected via the cord when the compression on the garment is adjusted. In other words, in order to adjust compression, there is no need for the wearer to separate a first panel from a second panel or disconnect the two panels. In this way, the embodiment of FIGS. 6A-6E is similar to the embodiments of FIGS. 1A-4B. Of course, in each of these embodiments, the fasteners used to connect the panels to one another while still allowing movement of the panels are different. Similar to other embodiments described above, the compression adjustment arrangement of FIGS. 6A-7B is configured to (i) retain the compression fabric of the shorts 10 at a first degree of stretch, (ii) increase the degree of stretch of the at least one fabric portion from the first degree of stretch to a second degree of stretch without releasing the at least one fabric portion from the first degree of stretch to a lesser degree of stretch, and (iii) retain the at least one fabric portion at the second degree of stretch.

Figure 8:
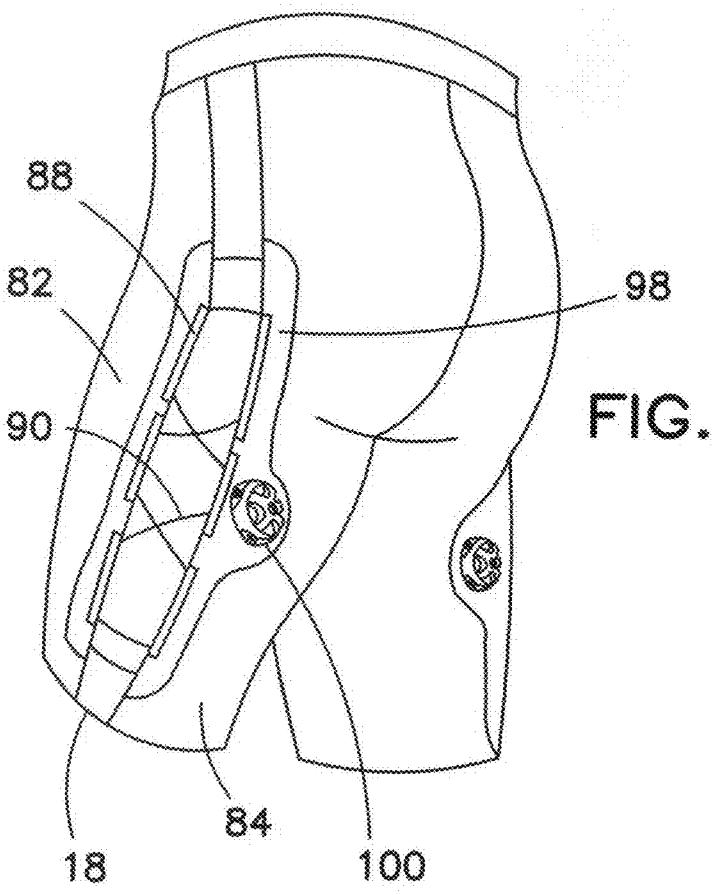
FIG. 8 shows a rear perspective view of an alternative embodiment of the adjustable compression shorts with lacing system of FIG. 6A.

With reference now to FIG. 8, an alternative embodiment of the adjustable lacing system 80 is shown where the cord adjustment mechanism 100 is placed in a different location on the garment. In particular, in the arrangement of FIG. 8, the cord adjustment mechanism 100 is situated near the center of the left leg portion 18 and the lacing eyestays 88 instead of near the bottom of the left leg portion 18 and the lacing eyestays 88. It will also be recognized that the cord adjustment mechanism 100 could also be placed on numerous other locations on the short 10.

Figure 9:
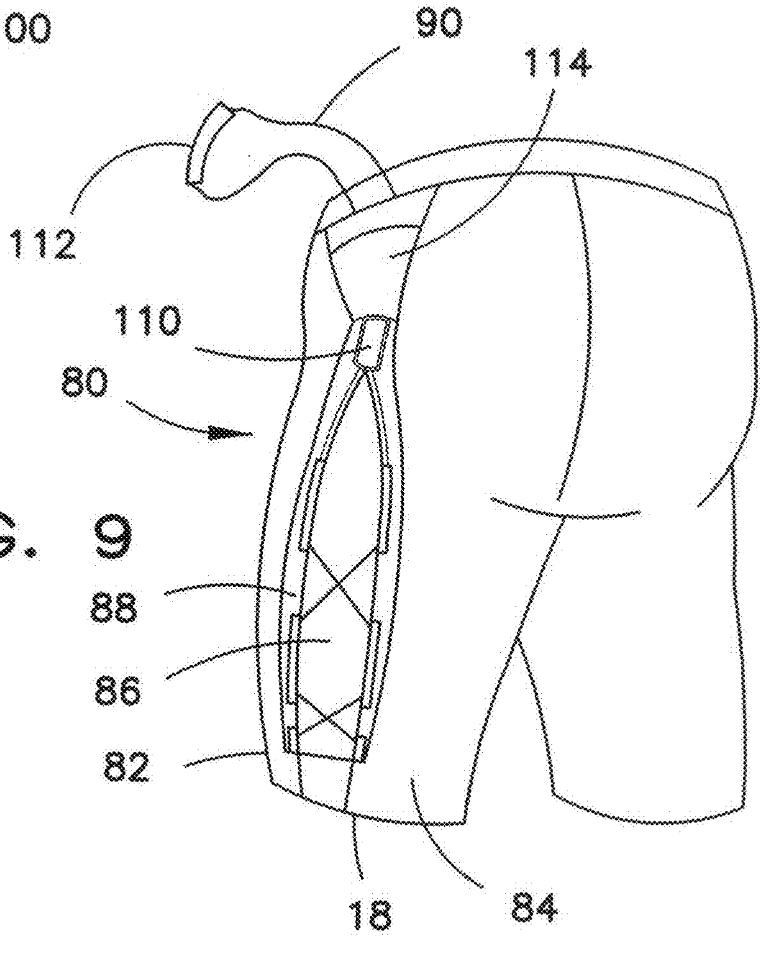
FIG. 9 shows a rear perspective view of another alternative embodiment of the adjustable compression shorts with the lacing system of FIG. 6A.

With reference now to FIG. 9, in an alternative embodiment of the adjustable lacing system 80, the cord 90 is adjusted using an alternative cord adjustment mechanism 100. In particular, in the embodiment of FIG. 9, the cord adjustment mechanism 100 includes a tensioner 110. The tensioner 110 includes a ratchet arrangement (not shown) that allows the cord 90 to be pulled through the tensioner 110 and not released until a release mechanism is activated. A handle 112 is provided on the cord 90 to assist a wearer in pulling on the cord 90. The handle 112 may be comprised of a relatively soft and flexible material. A pocket 114 configured to receive the handle 112 and cord 90 is provided on the shorts 10 along the side panel 86, just above the tensioner 110. In order to increase the compression provided on the leg portion 18, the user pulls the cord 90 away from the tensioner 110 using the handle 112. This causes a length of the cord 90 to pass through the tensioner 110, thus decreasing the effective length of the cord 90 threaded between the lacing eyestays 88, and increasing the compression provided by the front panel 82 and rear panel 84 of the shorts 10. In order to decrease the compression, the user depresses a release mechanism, thus allowing the cord 90 to pass back through the tensioner 110, increasing the effective length of the cord 90 threaded between the lacing eyestays 88, and decreasing the compression provided by the front panel 82 and rear panel 84 of the shorts 10.

Figure 10A:
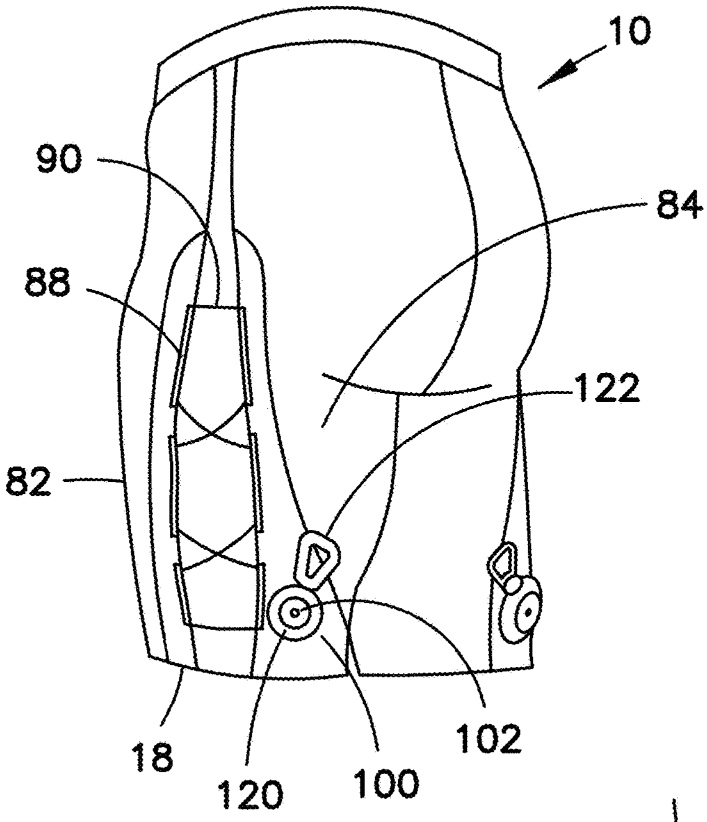
FIG. 10A shows a rear perspective view of another alternative embodiment of the adjustable compression shorts with the lacing system of FIG. 6A.
Figure 10B:
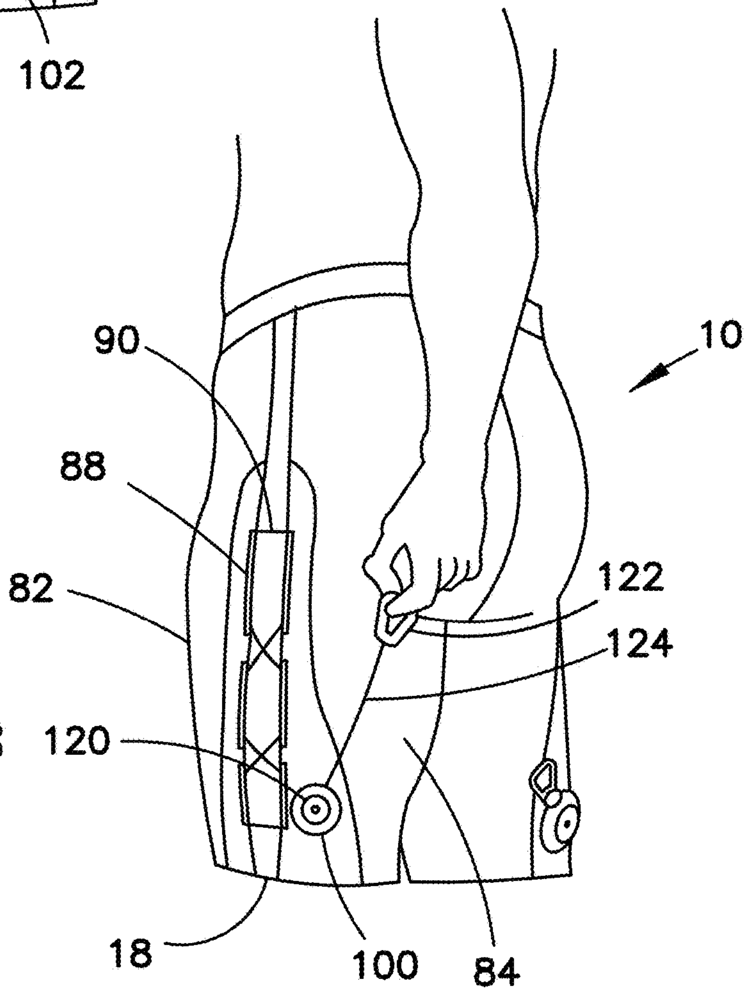
FIG. 10B shows a rear perspective view of the shorts of FIG. 10A with the cord adjustment mechanism being activated.

Yet another alternative embodiment of the adjustable lacing system 80 is shown in FIGS. 10A and 10B. This arrangement is similar to that of FIG. 6A, but the cord adjustment mechanism 100 includes a tensioner 120 that is rotated using a lawnmower-type pullstring arrangement instead of hand rotation of the dial 102. In this embodiment, a handle 122 is connected to a pullstring 124 that engages the spool (not shown). When the wearer pulls the handle 122 away from the tensioner 120, as shown in FIG. 10B, the pullstring 124 causes the spool to rotate in one direction, resulting in a length of cord 90 being reeled-in by the spool.

This also causes the front panel 82 and back panel 84 to be stretched, thus increasing the degree of compression provided by the shorts 10. When a release actuator is depressed (such as depression of the dial 102), the ratchet mechanism that locks the spool is released and the length of cord is released back to the lacing eyestays 88. This, in turn, reduces the amount of stretch on the front panel 82 and back panel 84 and reduces the compression provided by the shorts 10.

Still another alternative embodiment of adjustable compression garment of FIG. 1A is shown in FIGS. 11A-11J. In the embodiment of FIGS. 11A-11J, the adjustment mechanism for the compression short 10 is provided as an interval adjustment arrangement 140, where each adjustment interval offers a different degree of compression to a targeted muscle group.

Figure 11A:
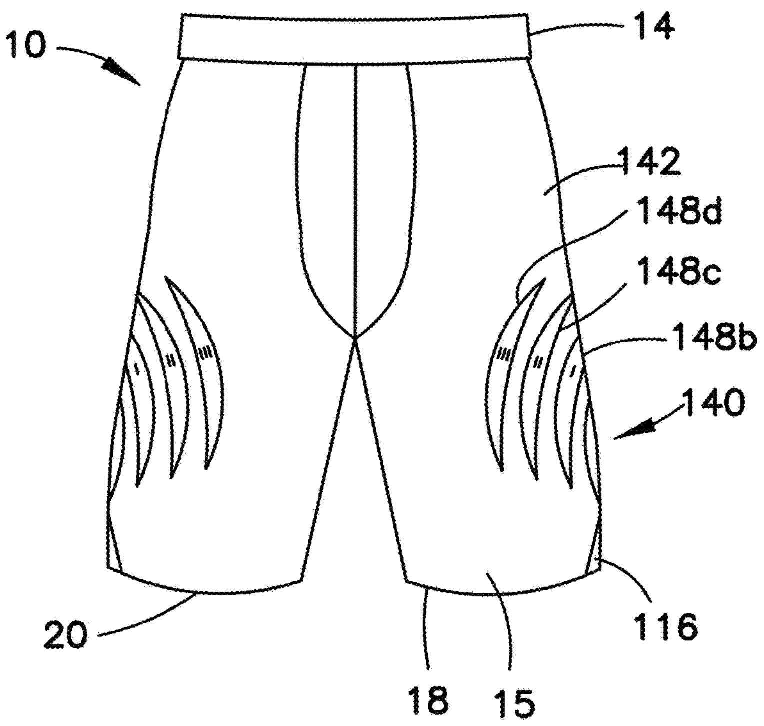
FIG. 11A shows a front view of another alternative embodiment of the adjustable compression shorts of FIG. 1A, where the adjustable compression arrangement is directed to the hamstring muscles.
Figure 11B:
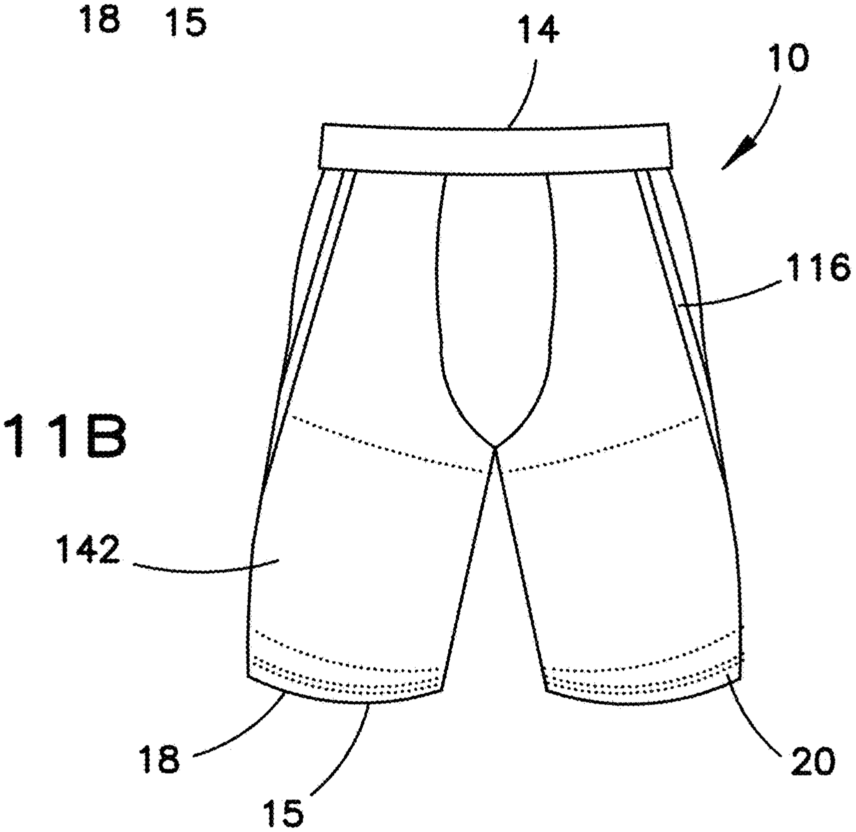
FIG. 11B shows a rear view of the adjustable compression shorts of FIG. 11A.
Figure 11D:
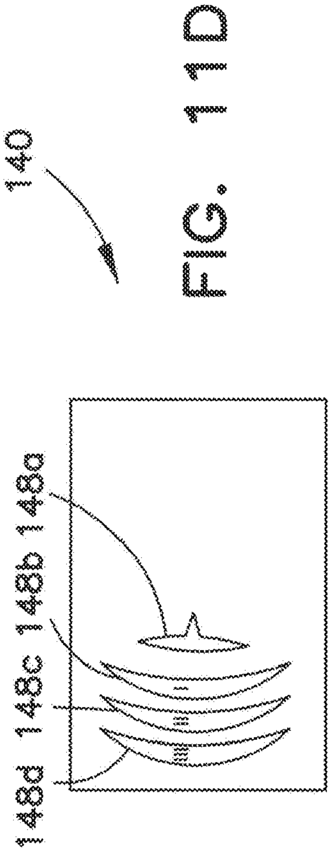
FIG. 11D shows an adjustment mechanism for the adjustable compression shorts of FIG. 11C with a middle elastic layer and top cover layer removed.
Figure 11E:
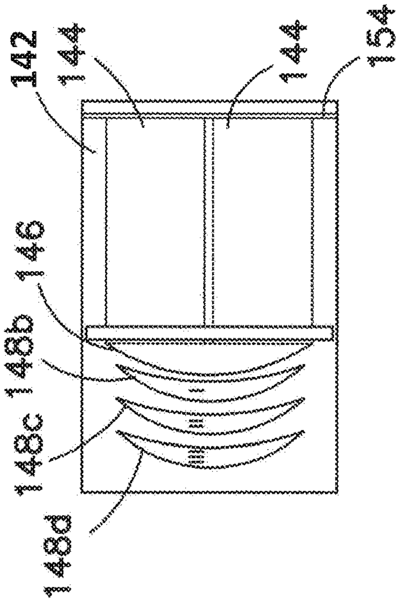
FIG. 11E shows the adjustment mechanism of FIG. 11D including the middle elastic layer.

As shown in FIG. 11E, the interval adjustment arrangement 140 comprises at least one elastic band 144 comprised of an elastic material that extends over the primary fabric layer 142 of the short 10 (which may also be referred to herein as the "base fabric layer"). Two elastic bands 144 are shown in the embodiment of FIG. 11E. Each elastic band 144 includes one end that is fixedly connected to the inseam 154 of the short 10 and an opposite end that is releasably connected to compression adjustment members in the form of docking pads 148. When the elastic bands 144 are stretched, the bands remain connected to the inseam 154 and stretch away from the inseam 154 thereby increasing the degree of compression provided by the elastic bands 144. However, in alternative embodiments, the elastic bands 144 may be connected to other positions on the short 10.

The elastic bands 144 are designed to cover a target compression area for the short 10. In the embodiment of FIGS. 11A-11J, the target compression area is the hamstring muscles. Thus, the elastic bands 144 extend across the back of each leg portion 18, 20 in a direction that is substantially transverse (perpendicular) to the direction of the hamstring muscle fibers. The elastic bands 144 are sufficiently wide to cover a substantial portion of the hamstring muscles. The elastic bands 144 may be comprised of any of numerous materials, such as elastomeric materials, polyester, nylon, combinations thereof, or compression fabrics. The elastic bands 144 may be oriented on the garment such that the main stretch direction of the elastic bands 144 is aligned with the direction in which the bands are pulled when adjusted for different levels of compression.

As shown in FIGS. 11C-11F, the adjustment mechanism 140 further includes a handle 146 connected to an end of each elastic band 144 opposite the inseam 154. The handle 146 is configured to be easily grasped by a wearer and pulled, thus allowing the wearer to extend the elastic bands 144 and increase compression, adding additional support to the targeted area. The handle 146 may be comprised of any of numerous materials, including textiles and plastic materials. In at least one embodiment, the handle 146 is comprised of a relatively soft and resilient elastomer such as polyurethane, which may be easily grasped by the wearer. FIG. 11G shows that the inside of the handle 146 includes a fastener member, such as a unidirectional hook member, with the hook members curving back toward the elastic band 144.

The handle 146 is configured to be releasably attached to any of a plurality of incrementally positioned docking pads 148*a-d*. Each of the docking pads 148*a-d* is positioned on the base fabric layer 142 of the short 10. This base fabric layer 142 may be a compression fabric, or any of various other types of fabric. Each of the docking pads 148*a-d* includes a complimentary fastening member configured to join to the fastening member of the handle 146. Thus, the docking pads 148*a-d* may include loop members configured to engage the unidirectional hook member of the handle 146. This unidirectional hook and loop fastening arrangement allows the user to increase compression by sliding the handle along the surface of the leg to the next incremental docking pad. In order to release the compression, the user may move the handle to a position in-between the docking pads 148*a-d*, pull the handle 146 away from the docking pads and base fabric layer 142, and move the handle 146 back toward the first docking pad 148*a*.

The docking pads 148*a-d* may be marked with indicia to indicate the level of compression offered at that particular docking pad. In the disclosed embodiment, the docking pads 148 are marked with a roman numbering system, I, II, III, where the docking pad 148*d*, marked with Roman numeral III is the tightest or highest compression offered. The docking pad 148*a* closest to the elastic member is a zero or normal level compression, and the elastic bands 144 do not offer any additional compression when the handle 146 is at this position (see FIG. 11F). FIG. 11H shows the handle 146 connected to docking pad 148*b* for the lowest level of compression. FIG. 11I shows the handle 146 connected to the docking pad 148*c* for the middle level of compression. FIG. 11J shows the handle 146 connected to the docking pad 148*d* for the highest level of compression.

Figure 11F:
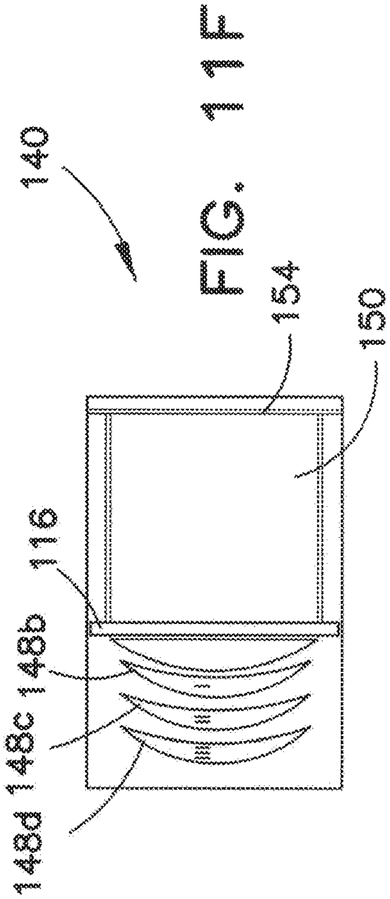
FIG. 11F shows the adjustment mechanism of FIG. 11E including the top cover layer.
Figure 11C:
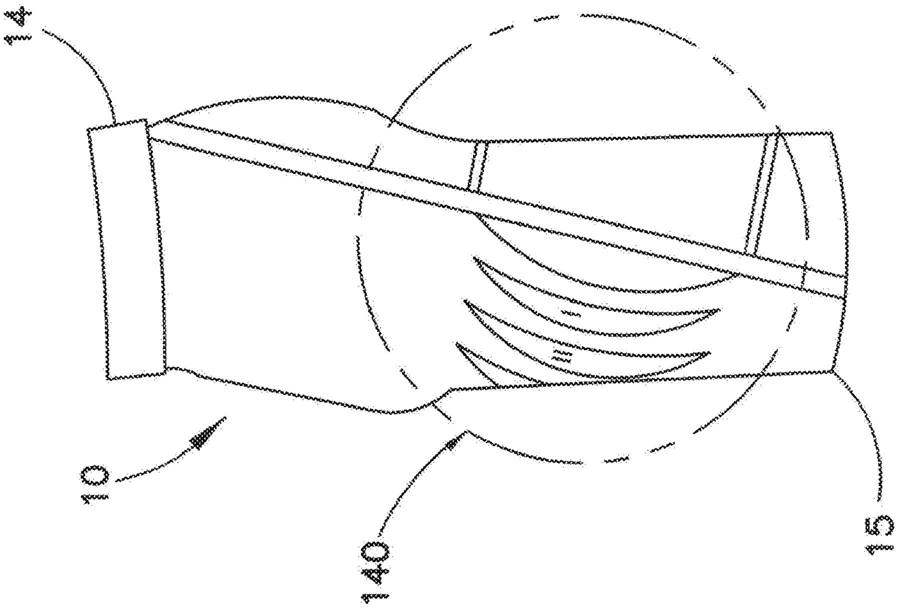
FIG. 11C shows a side view of the adjustable compression shorts of FIG. 11A.
Figure 11G:
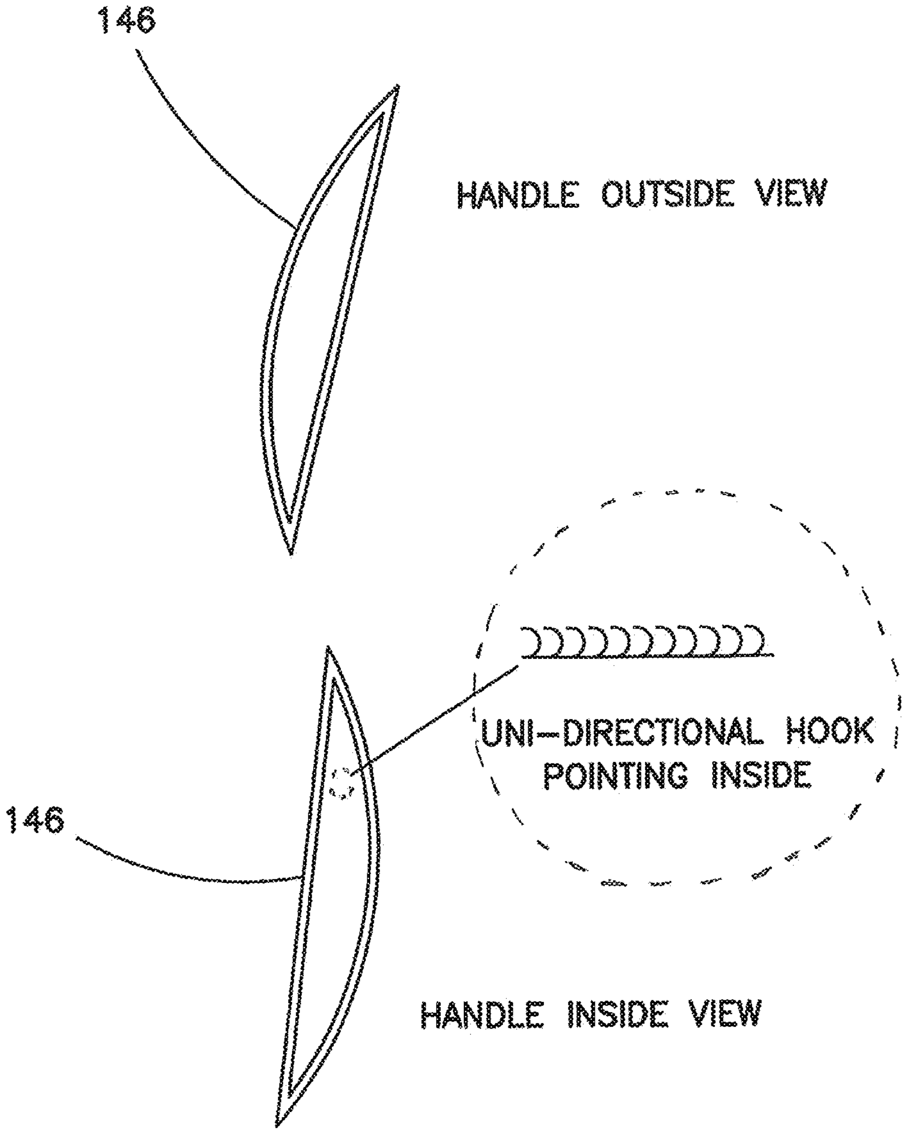
FIG. 11G shows a handle of the adjustment mechanism of FIG. 11F.
Figure 11H:
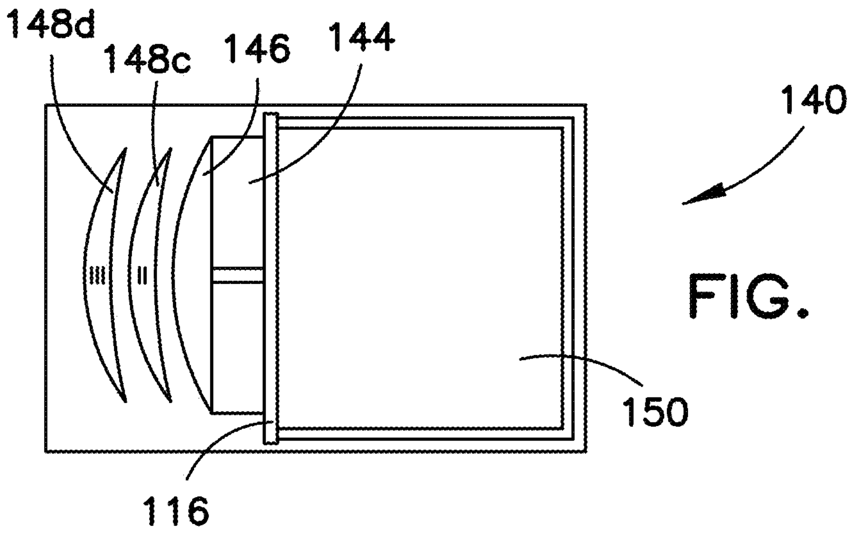
FIG. 11H shows the adjustment mechanism of FIG. 11F at a first compression level.
Figure 11I:
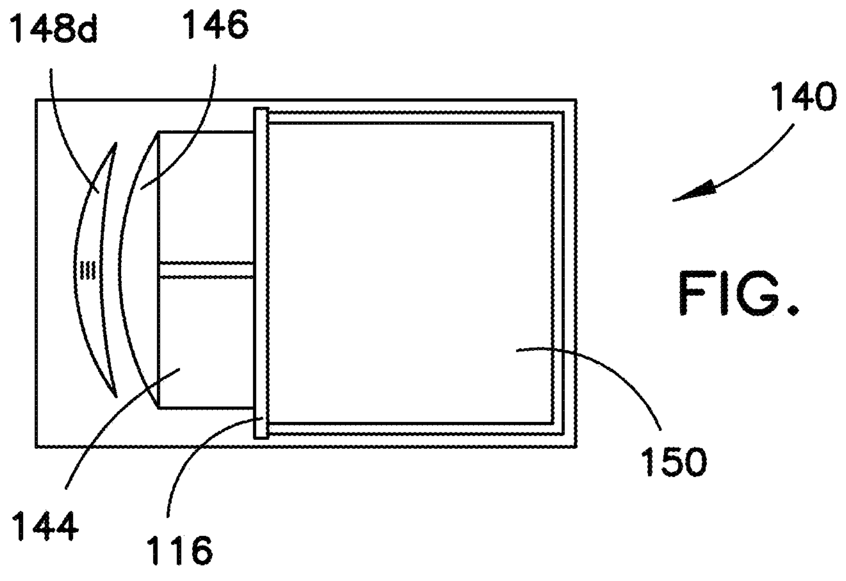
FIG. 11I shows the adjustment mechanism of FIG. 11F at a second compression level.
Figure 11J:
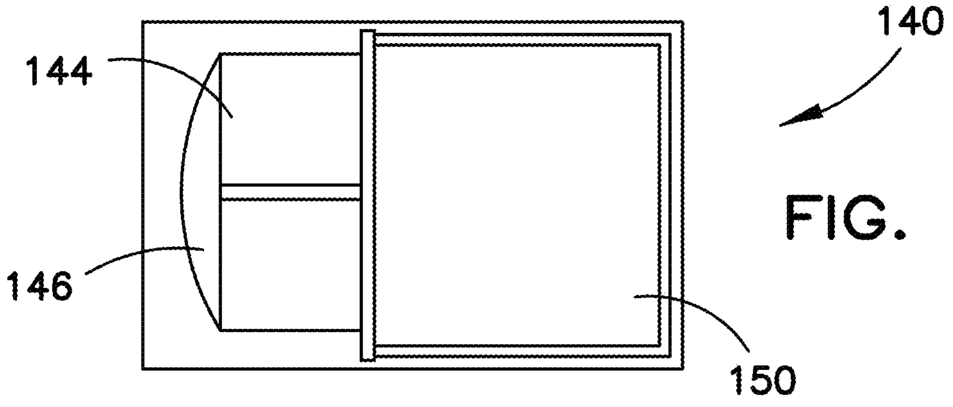
FIG. 11J shows the adjustment mechanism of FIG. 11F at a third compression level.

As shown in FIG. 11F, a cover layer 150 is provided over the elastic bands 144. The cover layer 150 forms a pocket around the bands 144 and conceals a major portion of the bands 144 on the shorts 10. In at least one embodiment, a bridge member 116 may be connected to the cover layer. The bridge member 116 generally extends across the elastic bands 144 and helps retain the bands 144 in a proper position on the garment. In at least one embodiment, the bridge member 116 may be comprised of an elastomeric material. In other embodiments, the bridge member may be a generally non-elastic material. It will also be recognized that in other embodiments, the cover layer 150 and/or the bridge member 116 may absent from the garment.

The bridge member 116 may be connected to the base fabric 142 at a position between the bands 144, thus providing a structure that extends across each of the bands 144 and helps maintain a separation between the bands 144. In the embodiment of FIGS. 11A-11J, the bridge member 116 extends the length of the shorts 10 from waist band 14 to cuff 15. However, in other embodiments, the bridge member 116 may only extend across the cover layer 150 (see, e.g., the embodiments of FIGS. 12A-C and 13A-C).

Figure 12B:
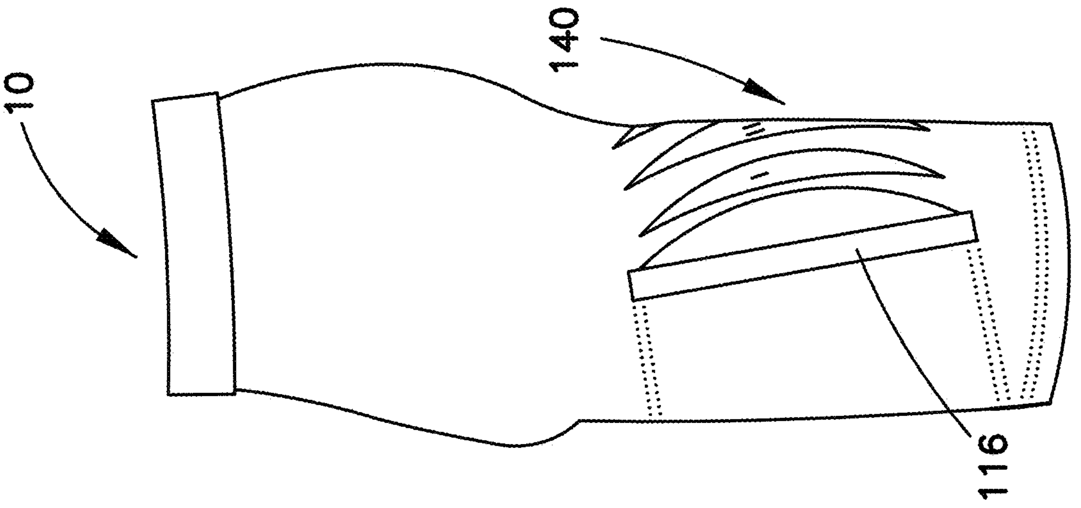
FIG. 12B shows a side view of the adjustable compression shorts of FIG. 12A.
Figure 12A:
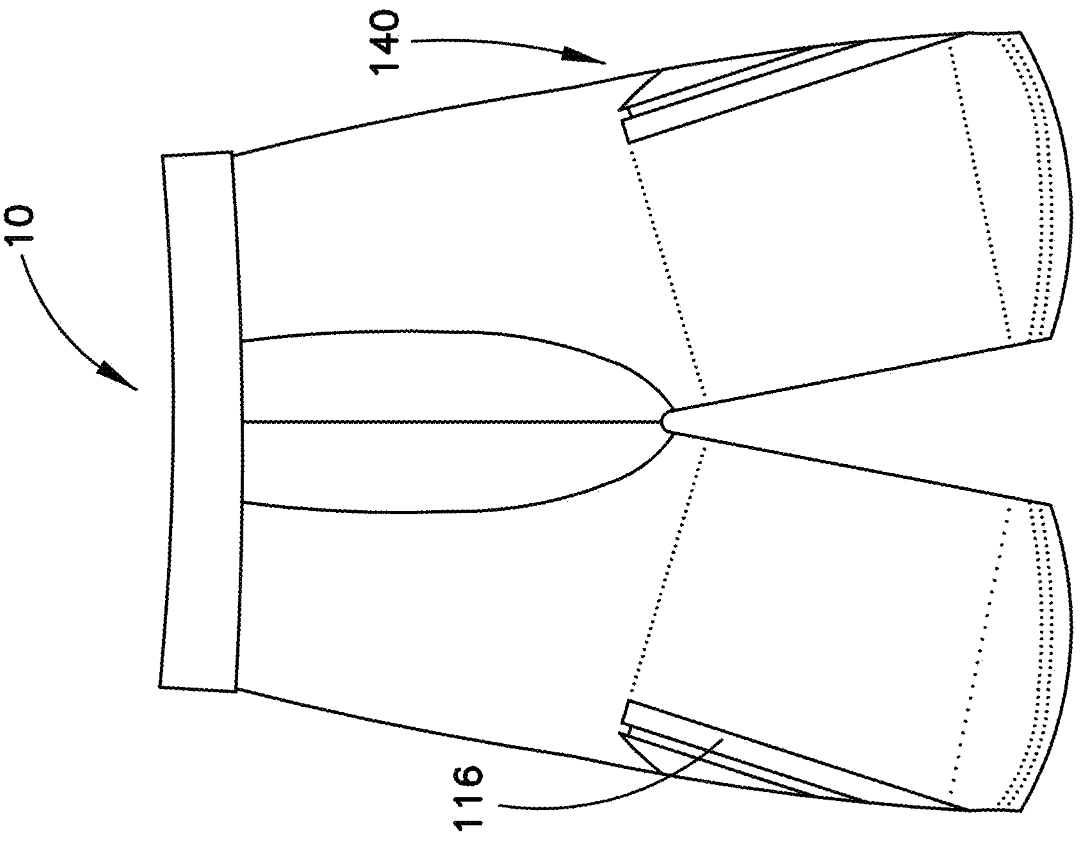
FIG. 12A shows a front view of an alternative embodiment of the adjustable compression shorts of FIGS. 11A-11J, where the adjustable compression arrangement is directed to the quadricep muscles.
Figure 12C:
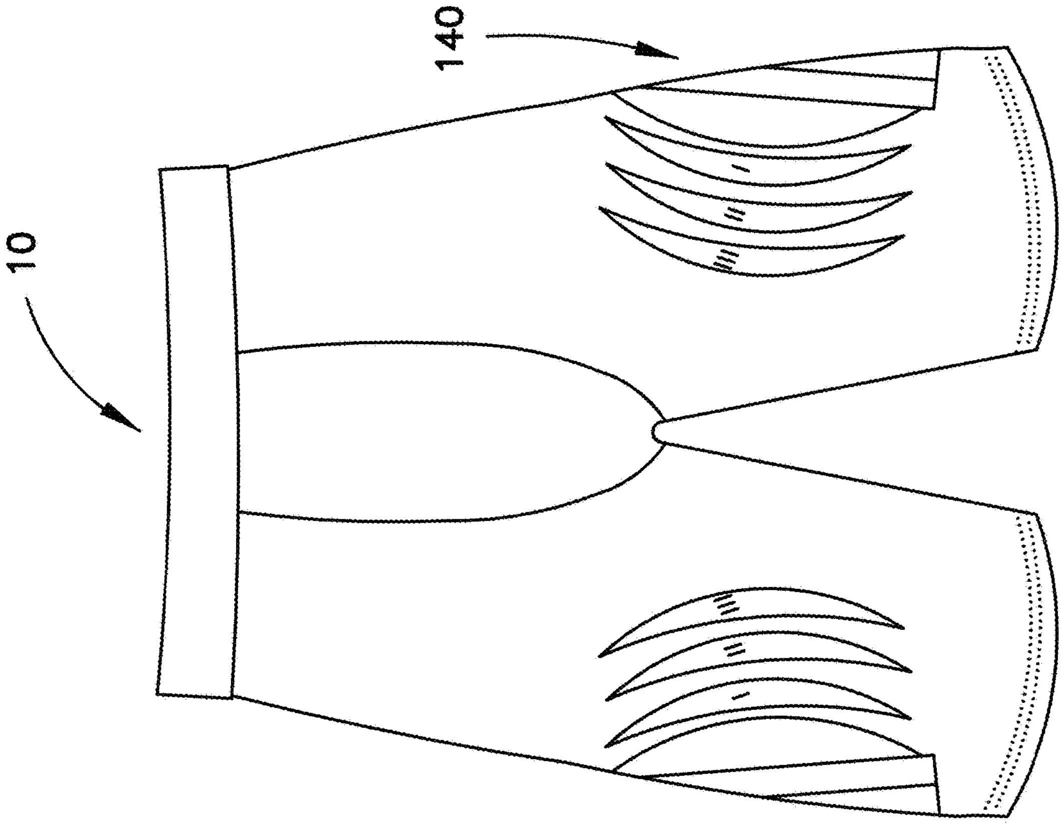
FIG. 12C shows a rear view of the adjustable compression shorts of FIG. 12A.
Figure 13A:
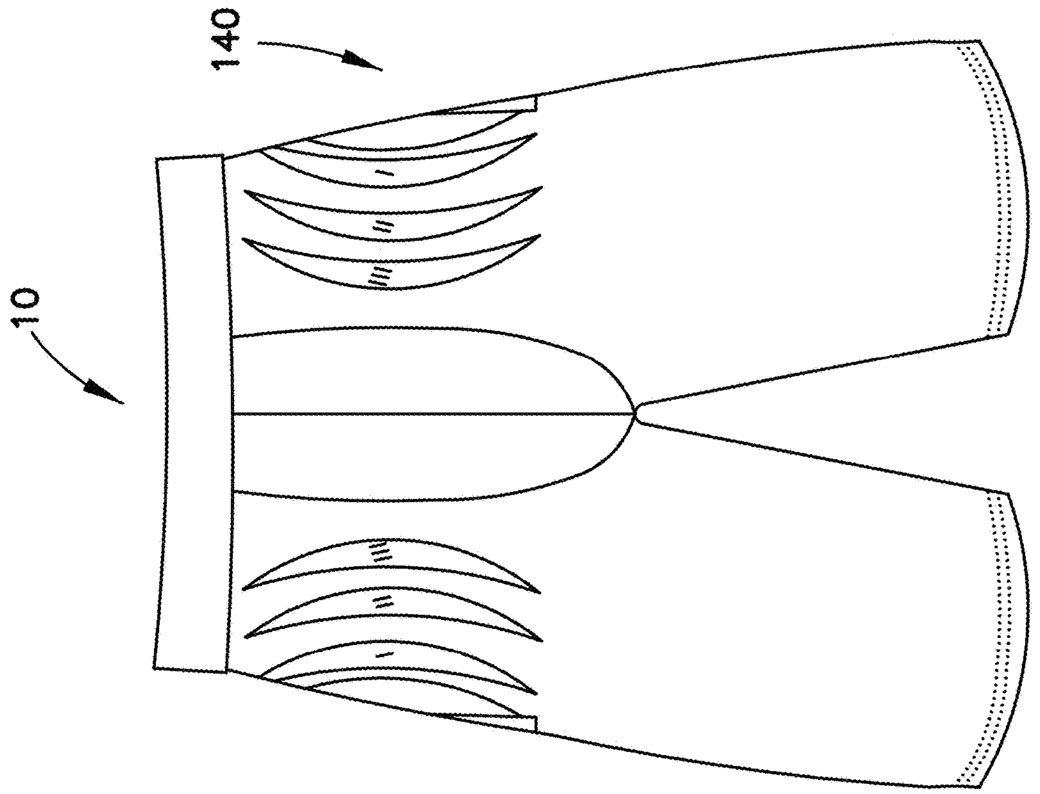
FIG. 13A shows a front view of an alternative embodiment of the adjustable compression shorts of FIGS. 11A-11J, where the adjustable compression arrangement is directed to the gluteus maximus muscles.
Figure 13B:
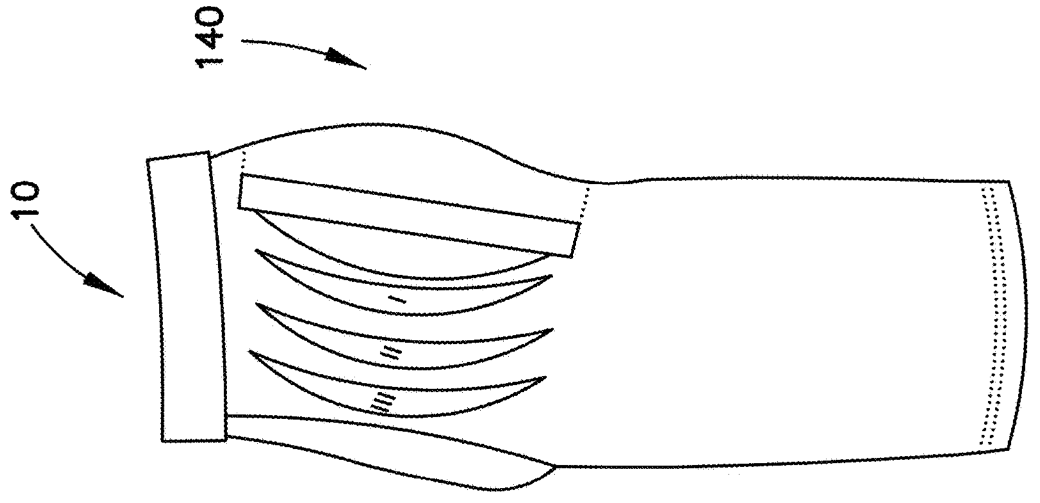
FIG. 13B shows a side view of the adjustable compression shorts of FIG. 13A.
Figure 13C:
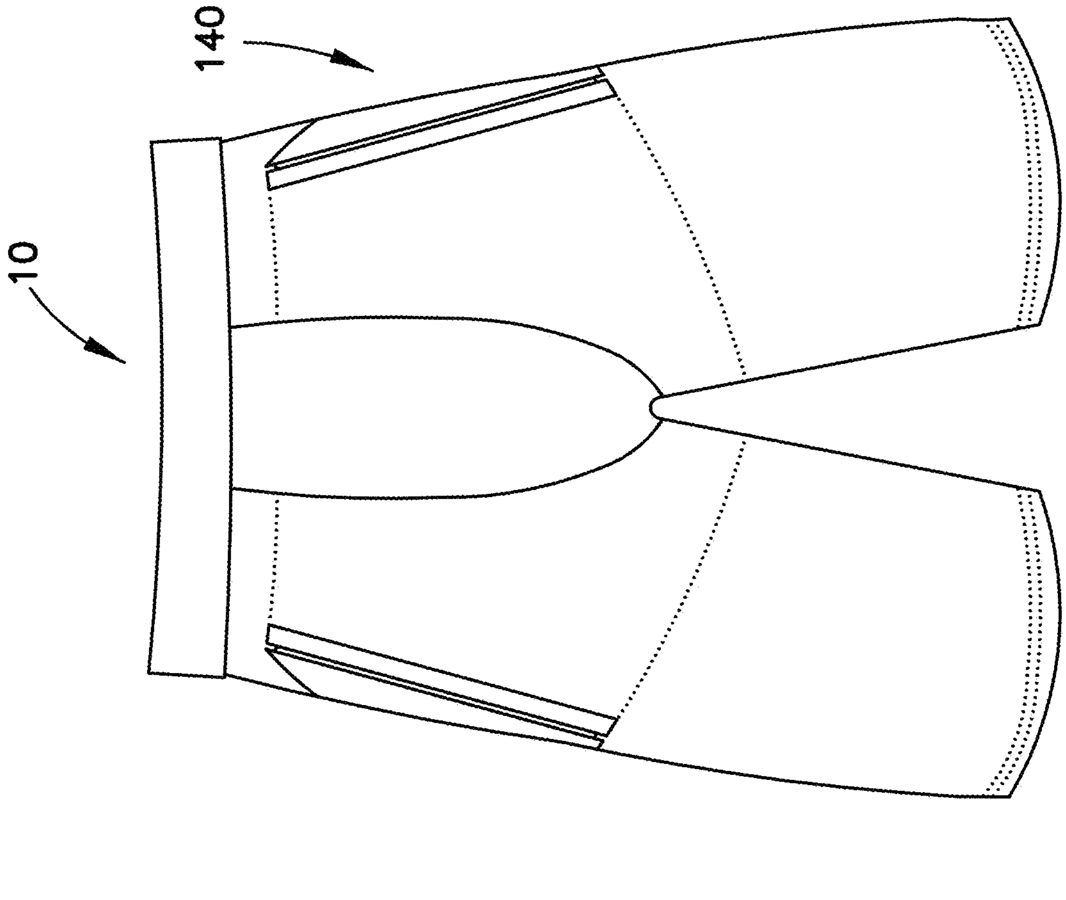
FIG. 13C shows a rear view of the adjustable compression shorts of FIG. 13A.

As mentioned above, in the embodiment of FIGS. 11A-11J, the target compression area is the hamstring muscles. However, the shorts or other garment may be arranged such that the target compression area is another muscle group on the lower body, such as, for example, the quadriceps, gluteus maximus, or calf muscles. FIGS. 12A-C show an alternative embodiment where the target compression area is the quadriceps. The adjustment mechanism 140 in this embodiment is the same as that shown in FIGS. 11A-J, but the adjustment mechanism is moved in order to provide compression to the anterior side of the short to target the quadriceps. Additionally, the bridge member 116 extends only across the cover 150 instead of the length of the short in the embodiment of FIGS. 12A-C. Similarly, FIGS. 13A-C show an alternative embodiment where the target compression area is the gluteus maximus. The adjustment mechanism 140 in this embodiment is the same as that shown in FIGS. 12A-C. In each of the disclosed embodiments, the muscle group is targeted and supported by having the wide elastic band 144 covering that area on the body thereby gaining the ability to give additional support through increasing compression. Each of these designs includes an embodiment where the compression adjustment mechanism utilizes unidirectional hook and loop fasteners.

Figure 14B:
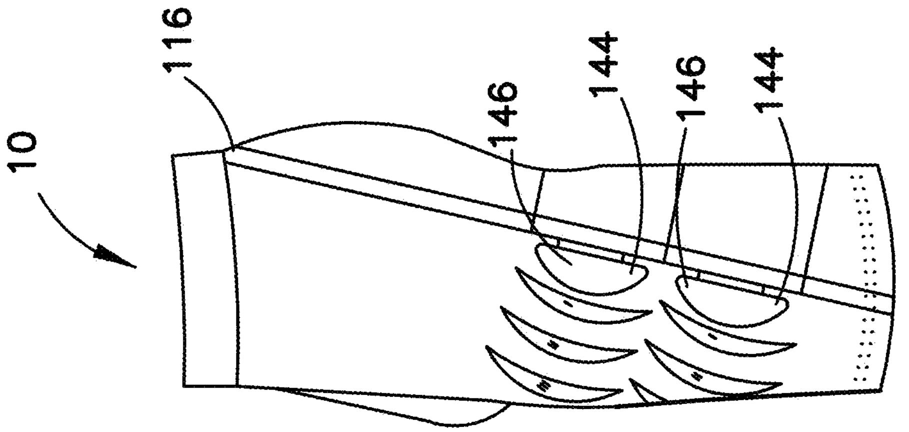
FIG. 14B shows a side view of the adjustable compression shorts of FIG. 14A.
Figure 14A:
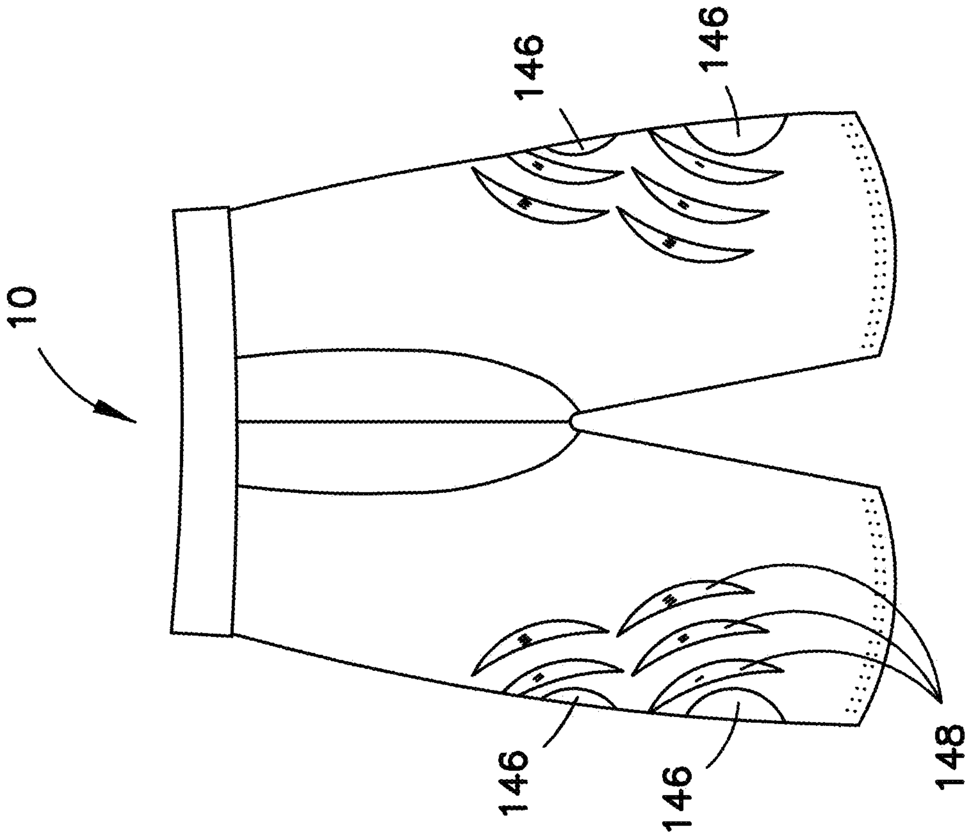
FIG. 14A shows a front view of an alternative embodiment of the adjustable compression shorts of FIGS. 11A-11J, where each band includes a separate handle.
Figure 14C:
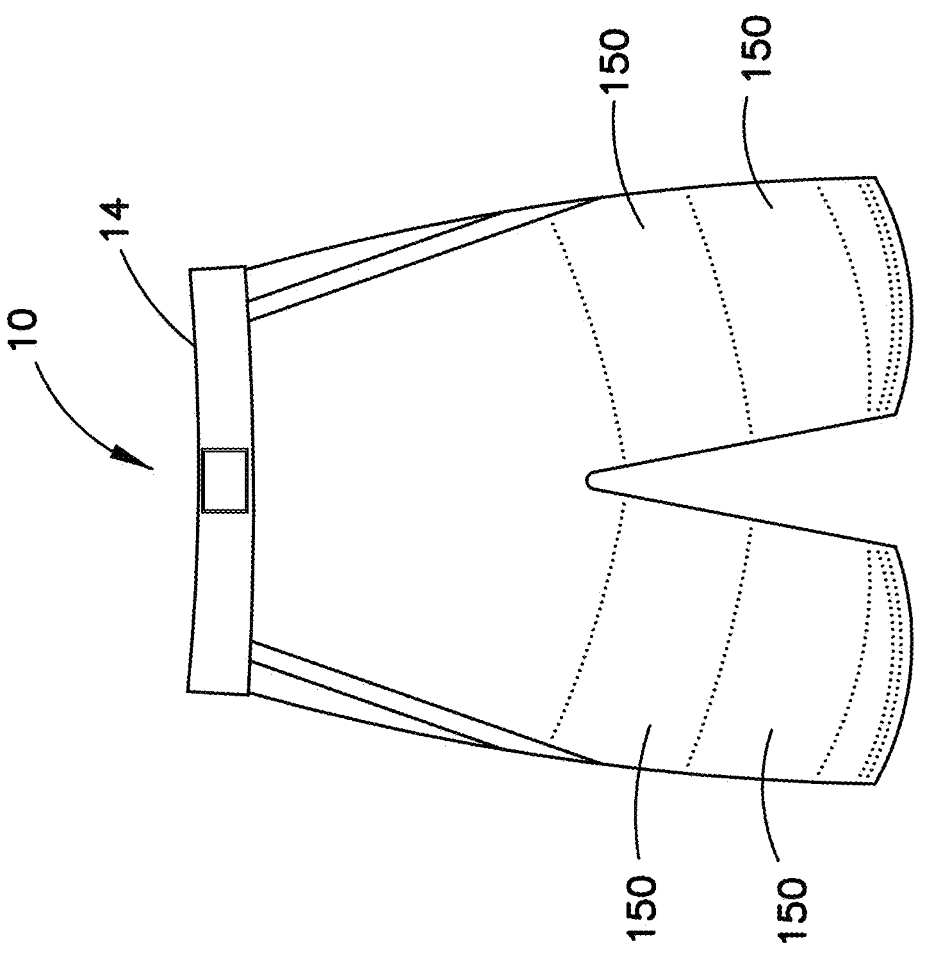
FIG. 14C shows a rear view of the adjustable compression shorts of FIG. 14A.

Another alternative embodiment of the garment is shown in FIGS. 14A-14C. This embodiment is similar to that of FIGS. 11A-11J, but in the embodiment of FIGS. 14A-14C, each of the bands 144 is connected to a separate handle 146. This allows the user to selectively adjust the compression of each band 144 within a muscle group. Accordingly, the user may choose to select an increased level of compression on a first band (e.g., a lower band), and lesser level of compression on a second band (e.g. an upper band) within a single muscle group. While FIGS. 14A-14C show two bands 144 and handles 146 for each hamstring, it will be recognized that any number of bands and handles may be provided for a given muscle group. In order to maintain separation between the bands 144, each band is positioned in separate sides of a split pocket in the embodiment of FIGS. 14A-14C.

Yet another alternative embodiment of the garment is shown in FIGS. 15A-15E. This embodiment is similar to that of FIGS. 14A-14C, but in the embodiment of FIGS. 15A-15E the base fabric material 142 on an anterior thigh portion 130 of the garment is comprised of a loop compatible fabric, such as a loop compatible stretch knit fabric. For example, the base fabric material 142 may be an unbroken loop tricot fabric weighing 7.5 oz./sq. yd. and including about 91% nylon and 9% spandex. This loop compatible fabric includes a plurality of loops integrally formed with the knit construction of the fabric, such that individual loops extend outward on the face of the fabric. This allows the fabric itself to provide a large fastener connection area for engagement with a unidirectional hook arrangement. Accordingly, docking pads (such as pads 148*a*-148*d* in the embodiment of FIG. 11A) are not included on the base fabric material 142 in the embodiment of FIGS. 15A-15E. However, it will be recognized that in at least one embodiment, indicia of a degree of compression provided by the bands may be included on the loop compatible fabric on the anterior thigh portion 130 of the shorts.

The handle 146 in the embodiment of FIGS. 15A-15E is provided by a reinforced foldover elastic portion on the ends of the elastic bands 144. A unidirectional hook fastener is provided on the inner side of the handle 146. This unidirectional hook fastener is similar to that shown in FIG. 11G. The unidirectional hook fastener is configured to engage the loops on the loop compatible fabric on the anterior thigh portion 130 of the shorts 10.

Similar to the embodiment of FIGS. 11A-11F, a cover layer 150 conceals the bands 144 on the rear portion of the shorts 10 in the embodiment of FIGS. 15A-15E. In particular, the cover layer 150 forms a pocket on the shorts and the bands 144 are received by and at least partially retained within the pocket. As particularly shown in FIGS. 15B and 15C, stitching 132 is provided on the cover layer 150 which splits the pocket into two distinct sides 140*a* and 140*b*, with each side of the pocket concealing one of the two bands 144. This split pocket arrangement keeps the bands 144 separated on the garment and facilitates independent use of each band 144. A bridge member 116 extends across the cover layer 150 at the openings to the pockets.

Figure 15B:
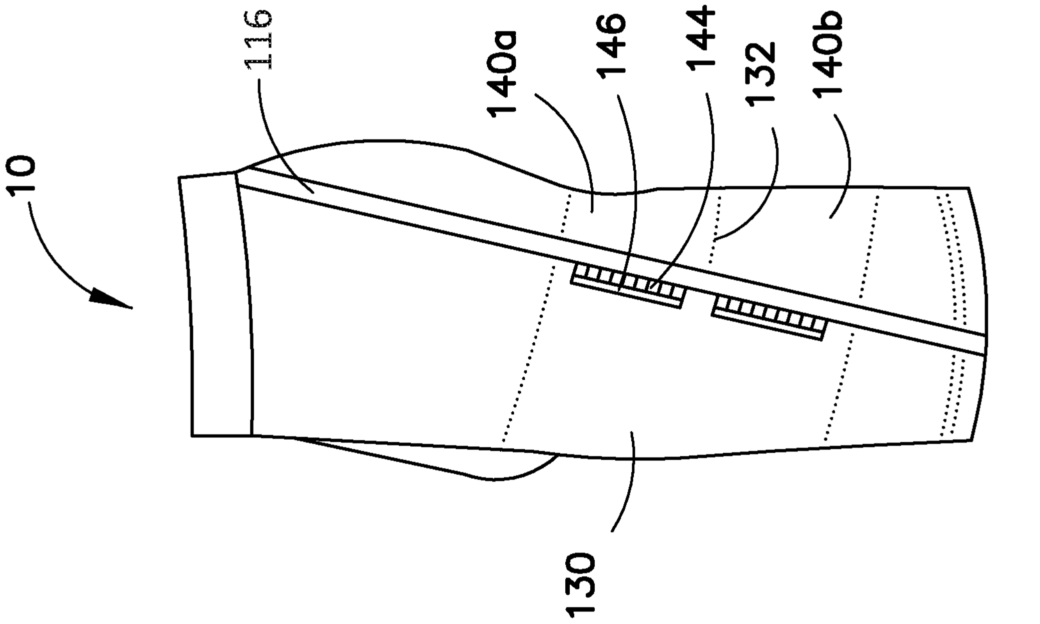
FIG. 15B shows a side view of the adjustable compression shorts of FIG. 15A.
Figure 15A:
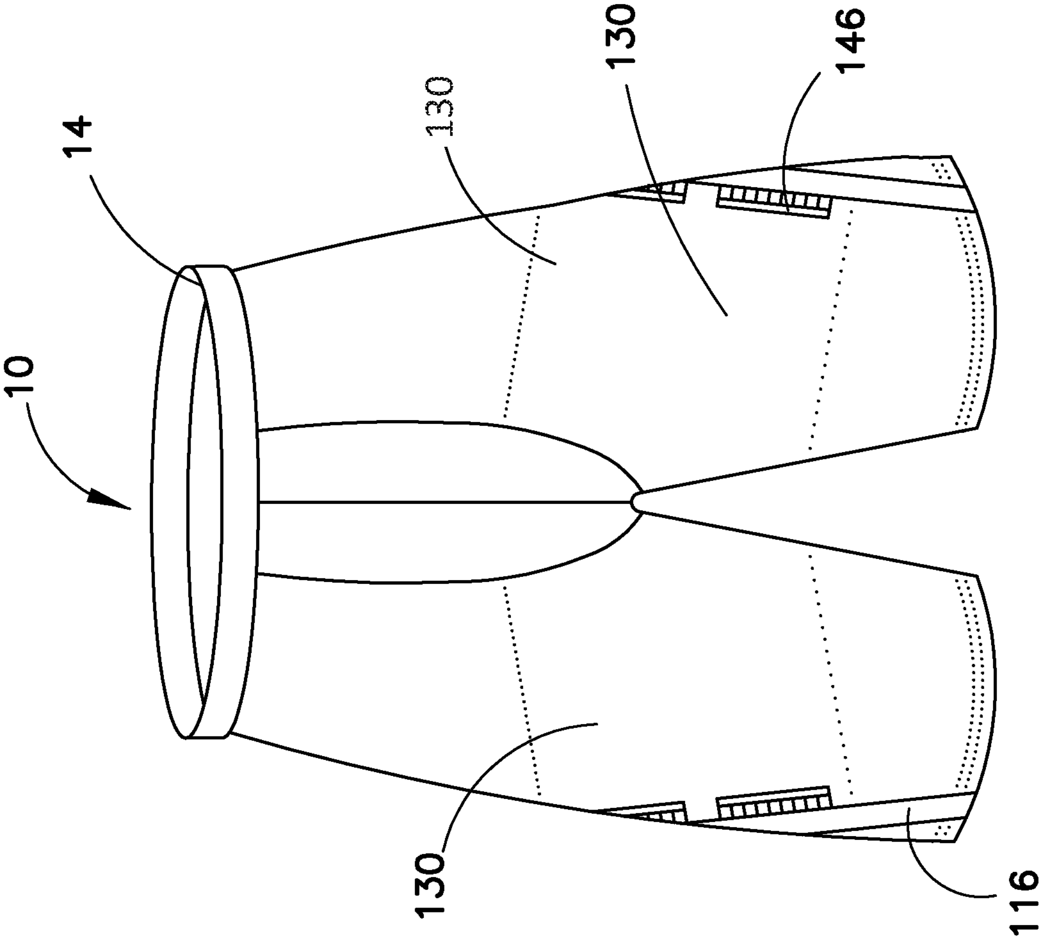
FIG. 15A shows a front view of yet another alternative embodiment of the adjustable compression shorts of FIGS. 11A-11J, where an anterior thigh portion is comprised of a loop compatible fabric.
Figure 15C:
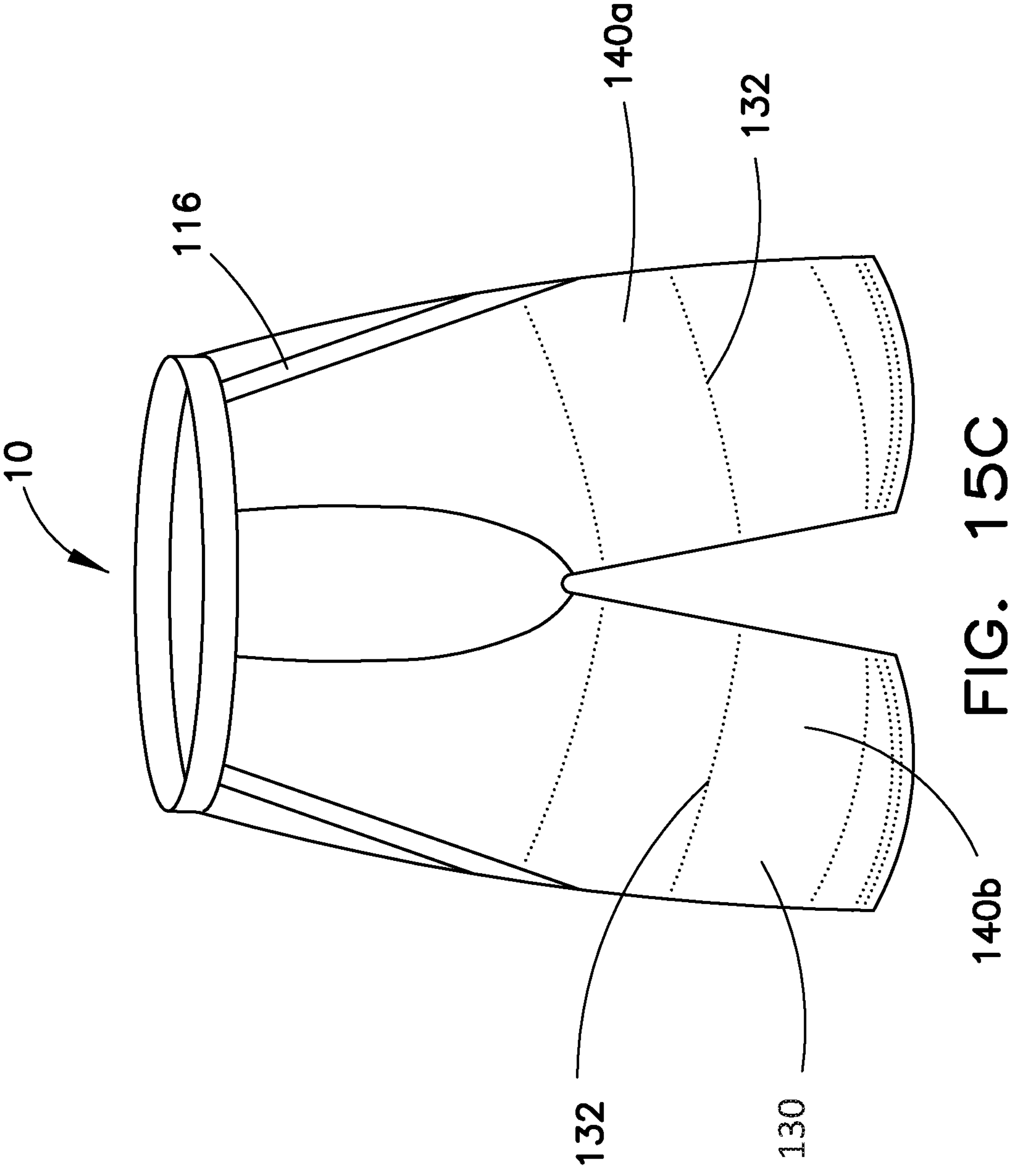
FIG. 15C shows a rear view of the adjustable compression shorts of FIG. 15A.
Figure 15D:
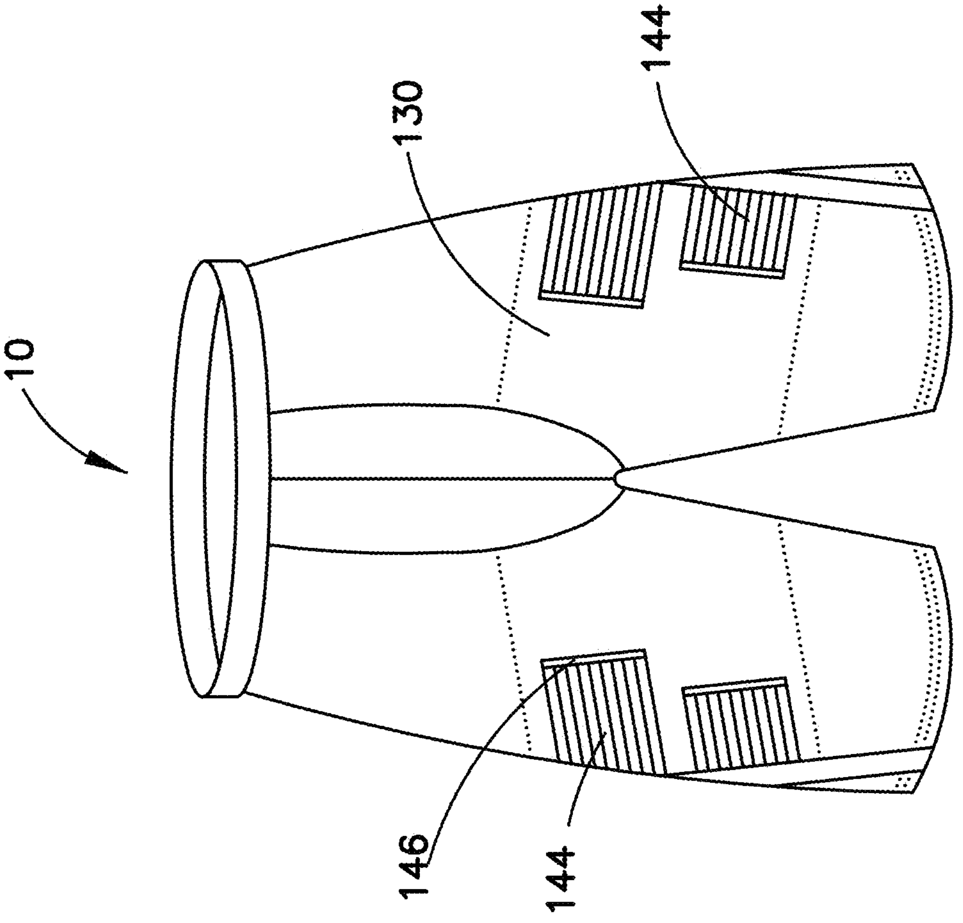
FIG. 15D shows a front view of the adjustable compression shorts of FIG. 15A with the elastic bands in an increased compression position.
Figure 15E:
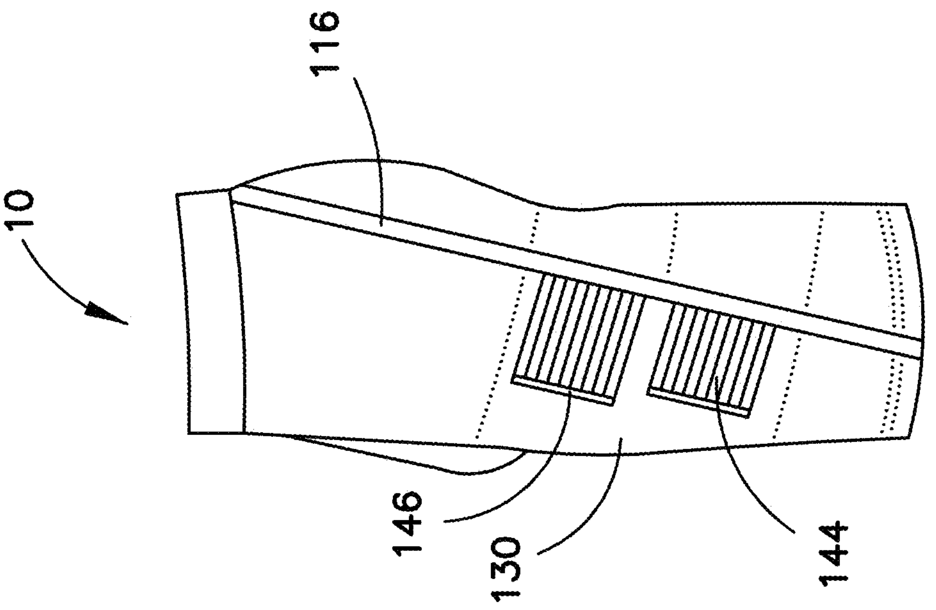
FIG. 15E shows a side view of the adjustable compression shorts of FIG. 15D.

In order to adjust the degree of compression provided by the garment, the wearer simply moves the handles 146 inward, sliding the unidirectional hooks on the underside of the handles across the loops provided by the loop compatible fabric of the anterior thigh portion 130. FIGS. 15D and 15E show the bands 144 in a stretched position on the garment with the attached handles 146 pulled inward (i.e., away from the bridge portion 116) in order to increase the degree of compression provided to the hamstring muscles of the wearer. In order to release the degree of compression, the wearer pulls the handles 146 away from the anterior thigh portion 130 and allows the elastic bands 144 to relax. Relaxation of the elastic bands 144 draws the attached handles 146 back toward the bridge portion 116. The handles 146 may then be reconnected to the loop compatible fabric with the elastic bands 144 providing a lesser degree of compression.

Figure 16A:
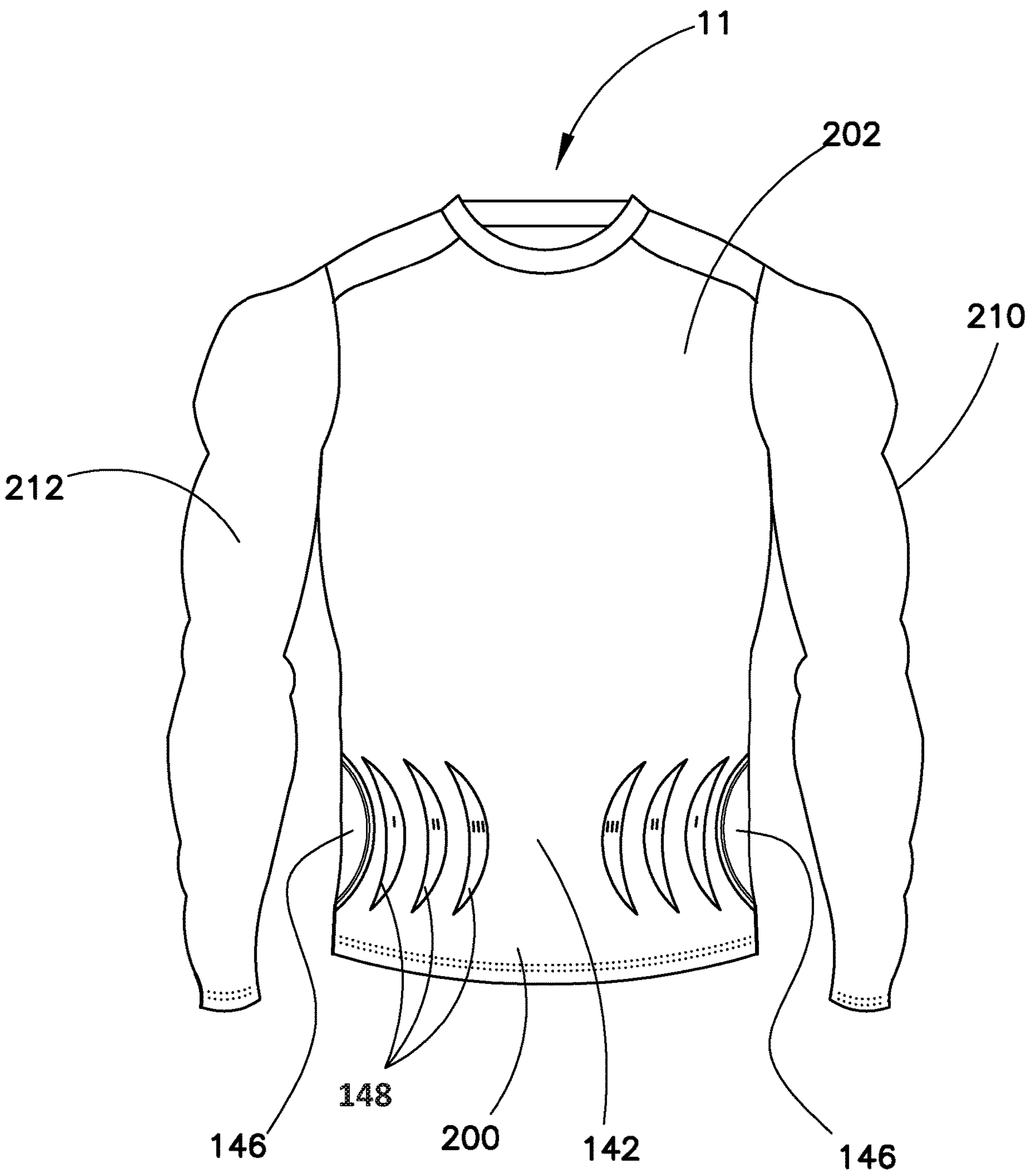
FIG. 16A shows a front view of an embodiment of the adjustable compression garment where the garment is a shirt having an adjustable compression arrangement similar to the embodiment of FIGS. 11A-11J.
Figure 16B:
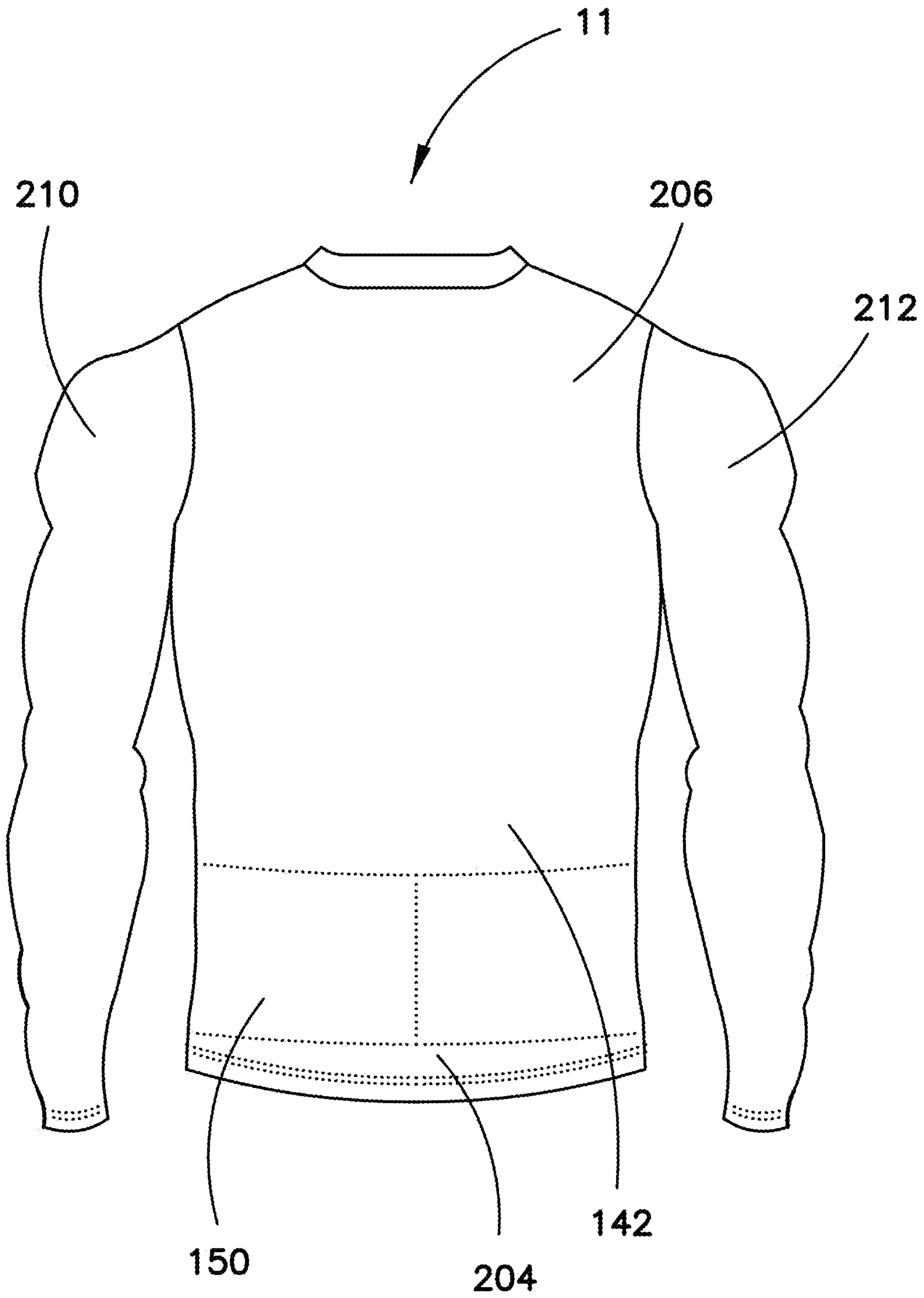
FIG. 16B shows a rear view of the adjustable compression shirt of FIG. 16A showing the cover layer of the adjustable compression arrangement.
Figure 16C:
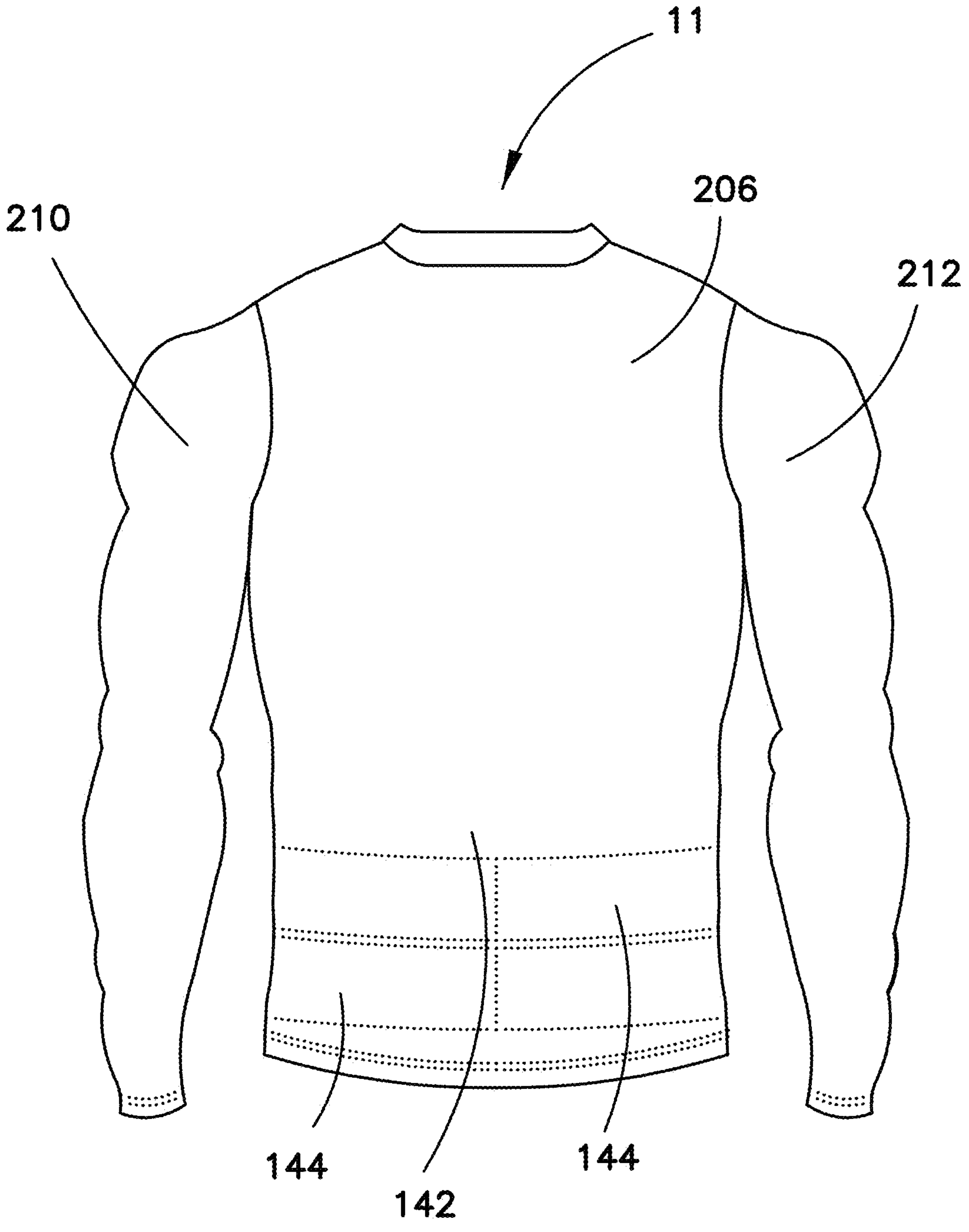
FIG. 16C shows a rear view of the adjustable compression shirt of FIG. 16A with the cover layer removed to expose the elastic bands of the compression arrangement.
Figure 16D:
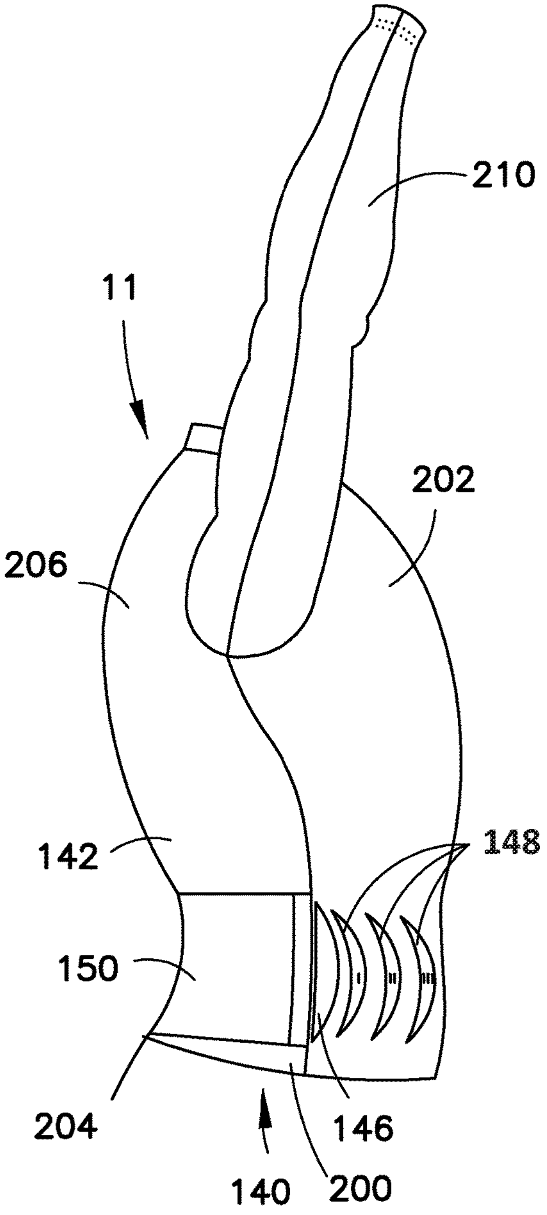
FIG. 16D shows a side view of the adjustable compression shirt of FIG. 16A with the elastic bands and handle in an un-stretched position.
Figure 16E:
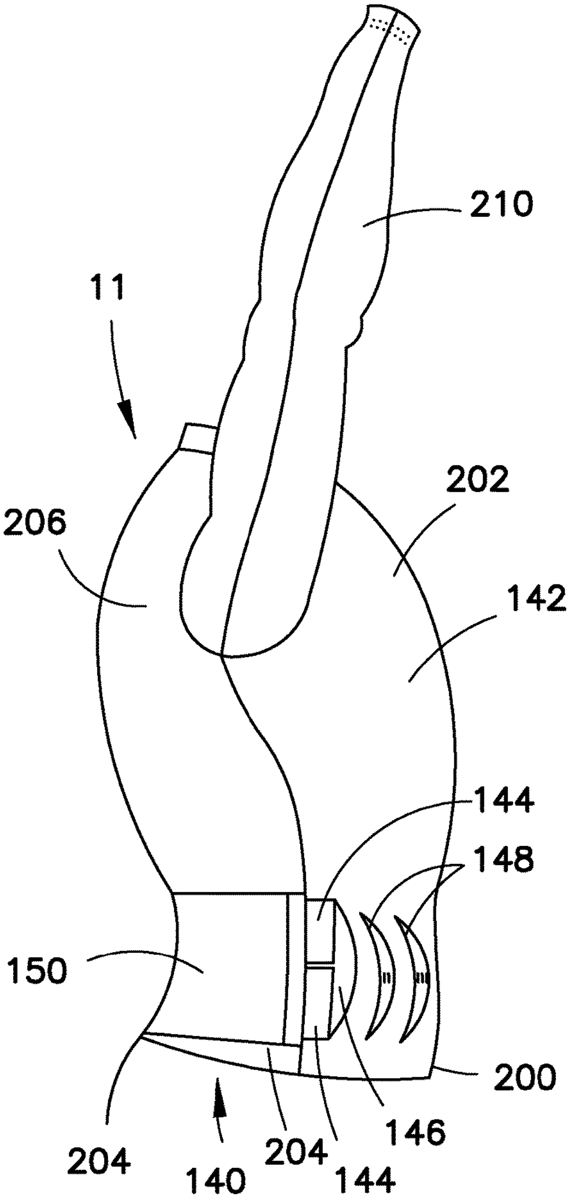
FIG. 16E shows a side view of the adjustable compression shirt of FIG. 16A with the elastic bands stretched to a first compression level.

While various embodiments of the adjustable compression garment have been described with respect to shorts in FIGS. 1-15, it will be recognized that the adjustable compression arrangement may also be provided on different garments, including shirts, sleeves, long pants, headgear, socks, shoes, or any other type of garment. In addition, the adjustable compression arrangement may be provided on a base layer, mid-layer, or inner layer of a garment, or on outerwear garments, including both tops and bottoms. An example of an alternative type of garment using the adjustable compression arrangement is shown in FIGS. 16A-16E. These figures show an adjustable compression arrangement on a shirt 11 with the adjustable compression arrangement directed to the muscles of the lower back. As shown in FIG. 16A, the shirt 11 comprises a torso portion including an abdomen portion 200, a chest portion 202, a lower back portion 204 and an upper back portion 206. The shirt 11 further comprises limb portions including a right arm portion 210 and a left arm portion 212. Docking pads 148 are provided on the abdomen portion 200 and are periodically positioned along the sides of the abdomen portion extending toward the center front portion of the garment. The elastic bands 144 are positioned on the lower back portion 204 of the garment with a cover layer 150 provided over the elastic bands 144, as shown in FIGS. 16B and 16C. Similar to the arrangement of FIGS. 11A-J, a user may adjust the level of compression by grasping the handles 146 and moving the handles to the docking pad 148 associated with the desired level of compression. For example, in FIG. 16D, the handles 146 are in a relaxed position, such that the elastic bands are unstretched. FIG. 16E shows the handles 146 moved to a first docking pad 148 associated with a first level of compression. It will also be recognized that in an alternative embodiment the garment of FIGS. 16A-16E may include a loop compatible fabric in lieu of the docking pads 148 in the abdominal area. Furthermore, although the targeted compression area in the embodiment of FIGS. 16A-16E is directed to the muscles of the lower back, the targeted compression area may be provided on any other portion of the shirt 11, including for example the abdomen, the arms, the upper back or the chest. Moreover, in other embodiments, different adjustable compression arrangements could be used to target various areas of the upper body.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A garment comprising:

a waistband;

a pelvis portion coupled to the waist portion;

a first panel coupled to the pelvis portion with a first lacing guide coupled to the first panel;

a second panel coupled to the pelvis portion with a second lacing guide coupled to the second panel, wherein at least one of the first panel and the second panel is comprised of an elastic material;

a cord extending between the first lacing guide and the second lacing guide; and a cord adjustment mechanism coupled to the cord, the cord adjustment mechanism configured to reduce an effective length of the cord extending between the first lacing guide and the second lacing guide and move the first panel closer to the second panel.

2. The garment of claim 1, the cord adjustment mechanism including a rotatable dial, wherein rotation of the dial reduces the effective length of the cord extending between the first lacing guide and the second lacing guide such that at least the first panel is stretched and an amount of compression provided by the garment to a wearer is increased.

3. The garment of claim 2 further comprising a third panel positioned between the first panel and the second panel, wherein the third panel is inelastic.

4. The garment of claim 3 further comprising a gusset coupling the third panel to at least one of the first panel and the second panel.

5. The garment of claim 1, wherein the garment is a short and the cord adjustment mechanism is located on a thigh portion of the short.

6. The garment of claim 2, the cord adjustment mechanism further including a cord release mechanism, wherein activation of the cord release mechanism increases the effective length of the cord extending between the first lacing guide and the second lacing guide such that the amount of compression provided by the garment to the wearer is decreased.

7. A garment comprising:

a first panel with a first lacing guide coupled to the first panel;

a second panel with a second lacing guide coupled to the second panel, wherein at least one of the first panel and the second panel is comprised of an elastic material;

a cord extending between the first lacing guide and the second lacing guide; and a cord adjustment mechanism coupled to the cord, the cord adjustment mechanism configured to reduce an effective length of the cord extending between the first lacing guide and the second lacing guide and move the first panel closer to the second panel, wherein the first panel extends from a limb portion to a torso portion of the garment and from a thigh portion to a buttocks portion of the garment.

8. A garment comprising:

at least one elastic panel with a first lacing guide and a second lacing guide coupled to the at least one elastic panel;

a non-elastic panel provided between the first lacing guide and the second lacing guide;

a cord extending between the first lacing guide and the second lacing guide and across the non-elastic panel; and a cord adjustment mechanism coupled to the cord, the cord adjustment mechanism configured to reduce an effective length of the cord extending between the first lacing guide and the second lacing guide and move the first lacing guide closer to the second lacing guide.

9. The garment of claim 8 wherein the cord adjustment mechanism includes a rotatable dial, wherein rotation of the dial reduces the effective length of the cord extending between the first lacing guide and the second lacing guide such that at least one elastic panel is stretched and an amount of compression provided by the garment to a wearer is increased.

10. The garment of claim 9 wherein the garment is a short and the rotatable dial is located on a thigh portion of the short.

11. The garment of claim 9 wherein the at least one elastic panel includes two elastic panels and wherein the non-elastic panel is positioned between the two elastic panels.

12. The garment of claim 11 further comprising a gusset coupling the non-elastic panel to the two elastic panels.

13. The garment of claim 9, the cord adjustment mechanism further including a cord release mechanism, wherein activation of the cord release mechanism increases the effective length of the cord extending between the first lacing guide and the second lacing guide such that the amount of compression provided by the garment to the wearer is decreased.

14. The garment of claim 8, wherein the at least one elastic panel extends from a limb portion to a torso portion of the garment and from a thigh portion to a buttocks portion of the garment.

15. A garment comprising:

a torso portion; and a leg extending from the torso portion, the leg comprising at least one elastic panel, a first lacing guide, and a second lacing guide;

a cord extending between the first lacing guide and the second lacing guide; and a dial positioned on the leg and coupled to the cord, the dial configured to increase an amount of compression provided by the at least one elastic panel by reducing an effective length of the cord extending between the first lacing guide and the second lacing guide and moving the first lacing guide closer to the second lacing guide.

16. The garment of claim 15 wherein the garment is a short and the dial is located on a thigh portion of the short.

17. The garment of claim 15 wherein the at least one elastic panel includes two elastic panels and wherein a non-elastic panel is positioned between the two elastic panels.

18. The garment of claim 15 wherein the dial is a rotatable dial coupled to the cord and the first lacing guide and the second lacing guide are located on a thigh portion of the garment.

19. The garment of claim 15 further including a cord release mechanism, wherein activation of the cord release mechanism increases the effective length of the cord extending between the first lacing guide and the second lacing guide such that the amount of compression provided by the garment to a wearer is decreased.

20. The garment of claim 15, wherein the at least one elastic panel extends from a limb portion to a torso portion of the garment and from a thigh portion to a buttocks portion of the garment.

* * * * *